US011227680B2

(12) United States Patent
Ambrose et al.

(10) Patent No.: US 11,227,680 B2
(45) Date of Patent: *Jan. 18, 2022

(54) SYSTEM AND METHOD FOR RANKING OPTIONS FOR MEDICAL TREATMENTS

(71) Applicant: ICPD Technologies, LLC, Schenectady, NY (US)

(72) Inventors: Paul G. Ambrose, Schenectady, NY (US); Sujata Bhavnani, Schecnectady, NY (US); Christopher M. Rubino, Schenectady, NY (US)

(73) Assignee: PRXCISION LLC, Schenectady, NY (US)

( * ) Notice: Subject to any disclaimer, the term of this patent is extended or adjusted under 35 U.S.C. 154(b) by 113 days.

This patent is subject to a terminal disclaimer.

(21) Appl. No.: 16/740,913

(22) Filed: Jan. 13, 2020

(65) Prior Publication Data

US 2020/0152307 A1    May 14, 2020

Related U.S. Application Data

(63) Continuation-in-part of application No. 14/600,948, filed on Jan. 20, 2015, now Pat. No. 10,534,895.

(51) Int. Cl.
*G16H 20/10* (2018.01)
*G16H 70/60* (2018.01)
(Continued)

(52) U.S. Cl.
CPC ........... *G16H 20/10* (2018.01); *G06F 3/0482* (2013.01); *G06F 3/04847* (2013.01);
(Continued)

(58) Field of Classification Search
CPC ........ G16H 20/10; G16H 70/60; G16H 70/20; G16H 10/60; G16H 20/30; G16H 50/50;
(Continued)

(56) References Cited

U.S. PATENT DOCUMENTS 7,286,970 B2 * 10/2007 Gardner ................. G16H 50/50
703/2
2007/0196479 A1 * 8/2007 Willmann .............. G16H 50/50
424/468

(Continued)

*Primary Examiner* — Eliza A Lam
(74) *Attorney, Agent, or Firm* — Heslin Rothenberg Farley & Mesiti P.C.

(57) ABSTRACT

A computer system, computer program product and method for determining a probability of attaining a PK-PD target associated with efficacy for a patient that includes a processor obtaining information identifying an infection and based on the information, generating and displaying, by the one or more processors, a list comprising one or more pathogens consistent with the information, the processor then obtaining a first indication designating at least one pathogen from the list comprising one or more pathogens and based on at the obtaining of the least one pathogen, generating a list comprising one or more drug therapies utilized to treat the at least one pathogen. The method also includes the processor obtaining, descriptive information relating to a patient and based on the one or more drug therapies, selecting a pharmacokinetic model and the processor applying the pharmacokinetic model and utilizing the information relating to the patient to determine, for each of the one or more drug therapies, a probability of attaining a PK-PD target associated with efficacy for the patient with the infection.

19 Claims, 33 Drawing Sheets

(51) Int. Cl.
*G16H 70/20* (2018.01)
*G16H 10/60* (2018.01)
*G16H 50/50* (2018.01)
*G06F 3/0482* (2013.01)
*G06F 3/0484* (2013.01)
*G16H 20/30* (2018.01)
*G16H 10/40* (2018.01)

(52) U.S. Cl.
CPC .............. *G16H 10/40* (2018.01); *G16H 10/60* (2018.01); *G16H 20/30* (2018.01); *G16H 50/50* (2018.01); *G16H 70/20* (2018.01); *G16H 70/60* (2018.01)

(58) Field of Classification Search
CPC ........ G16H 10/40; G16H 70/40; G16H 50/20; G06F 3/04847; G06F 3/0482
See application file for complete search history.

(56) References Cited

U.S. PATENT DOCUMENTS

2008/0080570 A1* 4/2008 Murison ............. H01S 3/06754
372/20
2012/0197188 A1* 8/2012 Syroid ................... G16H 50/50
604/93.01

* cited by examiner

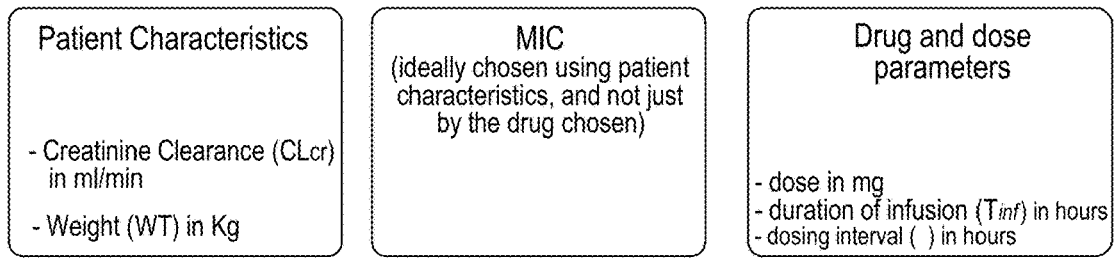

Compute time above MIC

① Compute $K_{cp}$, $K_{pc}$, $K_{el}$

② Compute alpha, beta

③ Compute A, B

④A Compute $fC(t)$: Concentration during infusion; specifically, to find the single root of this equation. This is $t_1$ ④B Compute $fC(t)$: Concentration after infusion; specifically, to find the single root of this equation. This is $t_2$ ⑤ Compute final number: Time above MIC, as a percentage, using the formula (where τ is the dosing interval):

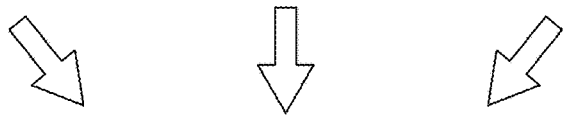

Algebraic Approach (a simplification to the more robust approach that would employ Differential Calculus)

Result: Target Attainment (as a single percentage value)

EXAMPLE DRUG: MEROPENEM

*TWO-COMPARTMENTAL MODEL:*

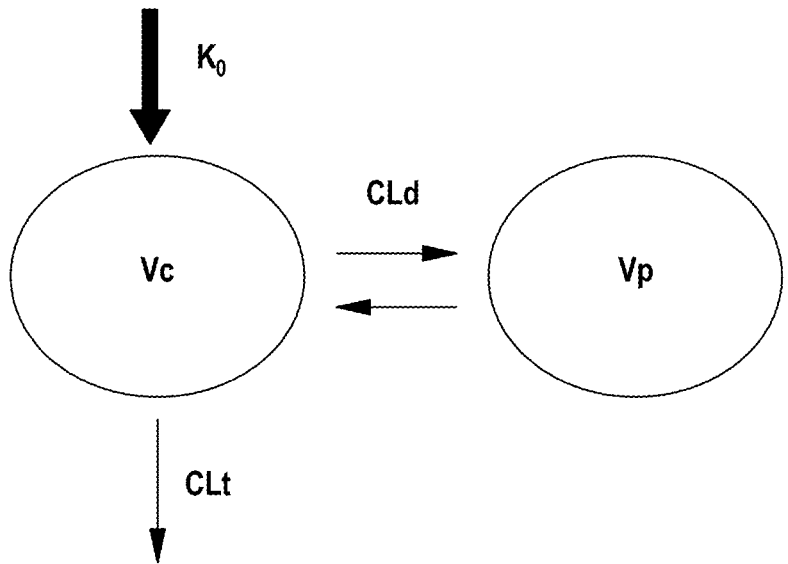

*Equations for intermittent infusion at steady state using two compartmental model:*

- During infusion: where $0 \leq t \leq T_{inf}$
  - $fC(t) =$
  $$f_{up} \times K_0 \left[ \frac{A}{\alpha}\left(1 - e^{-\alpha t} + e^{-\alpha \tau} \frac{\left(1-e^{-\alpha T_{inf}}\right) e^{-\alpha(t-T_{inf})}}{1 - e^{-\alpha \tau}}\right) + \frac{B}{\beta}\left(1 - e^{-\beta t} + e^{-\beta \tau} \frac{\left(1-e^{-\beta T_{inf}}\right) e^{-\beta(t-T_{inf})}}{1 - e^{-\beta \tau}}\right) \right]$$

- After infusion: where $T_{inf} \leq t \leq \tau$
  - $fC(t) = f_{up} \times K_0 \left[ \frac{A}{\alpha}\left(\frac{\left(1-e^{-\alpha T_{inf}}\right) e^{-\alpha(t-T_{inf})}}{1 - e^{-\alpha \tau}}\right) + \frac{B}{\beta}\left(\frac{\left(1-e^{-\beta T_{inf}}\right) e^{-\beta(t-T_{inf})}}{1 - e^{-\beta \tau}}\right) \right]$ The parameters are:

| $A = \frac{1}{Vc}\frac{\alpha - Kpc}{\alpha - \beta}$ | $B = \frac{1}{Vc}\frac{\beta - Kpc}{\beta - \alpha}$ |
|---|---|

FIG 23 (con)

| $\alpha = \frac{1}{2}\left[(Kcp + Kpc + Kel) + \sqrt{(Kcp + Kpc + Kel)^2 - 4(Kpc)(Kel)}\right]$ | $\beta = \frac{1}{2}\left[(Kcp + Kpc + Kel) - \sqrt{(Kcp + Kpc + Kel)^2 - 4(Kpc)(Kel)}\right]$ | |
|---|---|---|
| $Kcp = \frac{CLd}{Vc}$ | $Kpc = \frac{CLd}{Vp}$ | $Kel = \frac{CLt}{Vc}$ |

*For example for the drug meropenem:*

- Vc (Liters) = 10.8 x (WT/70)
- Vp (Liters) = 12.6 x (WT/70)
- CLd (Liters/hour) = 18.6 x (WT/70)
- CLt (Liters/hour) = (10.2 + 2.08 x CLcr) x (WT/70) x 0.06
- fraction unbound (fup) = 0.98

Pseudo-code for finding roots:

Step 1: Test for special cases at steady-state:

Step 2: Compute fCmin if fCmin > MIC then %fT>MIC = 100%
STOP

Step 3: Compute fCmax if fCmax < MIC then %fT>MIC = 0%
STOP

Step 4: Else, compute t1 and t2

Step 5: Compute t1 (the time to go from fCmin to MIC Compute T2) using algorithm

Step 6: Compute t2 (time to go from fCmax to MIC) using algorithm

Step 7: Compute %fT>MIC:

%fT>MIC = (t2-t1) /Tau x 100

Inputs:

FIG 23 (con)

- Drug: meropenem example
  - Dose = 2000 milligrams
  - Duration of infusion ($T_{inf}$) = 3 hours
  - $K_o$ = Dose/$T_{inf}$ = 2000 mg/3hr
  - Dosing interval ($\tau$) = 8 hours
- Patient characteristics:
  - Creatinine clearance (CLcr) = 63.4 ml/min
  - Weight (WT) = 86 kg
  - MIC = 8 mg/L Calculations:

- Vc = 10.8 x (86/70) = 13.2 L
- Vp = 12.6 x (86/70) = 15.48 L
- Cld = 18.6 x (86/70) = 22.8 L/hr
- Clt = (10.2 + 2.08 x 63.4) x (86/70) x 0.06 = 10.5 L/hr $$Kcp = \frac{CLd}{Vc} = \frac{22.8}{13.2} = 1.73$$

$$Kpc = \frac{CLd}{Vp} = \frac{22.8}{15.48} = 1.47$$

$$Kel = \frac{CLt}{Vc} = \frac{10.5}{13.2} = 0.796$$

$$\alpha = \frac{1}{2}\left[(Kcp + Kpc + Kel) + \sqrt{(Kcp + Kpc + Kel)^2 - 4(Kpc)(Kel)}\right]$$

$$= \frac{1}{2}\left[(1.73 + 1.47 + 0.796) + \sqrt{(1.73 + 1.47 + 0.796)^2 - 4(1.47)(0.796)}\right]$$

$$= 3.677$$

$$\beta = \frac{1}{2}\left[(Kcp + Kpc + Kel) - \sqrt{(Kcp + Kpc + Kel)^2 - 4(Kpc)(Kel)}\right]$$

$$= \frac{1}{2}\left[(1.73 + 1.47 + 0.796) + \sqrt{(1.73 + 1.47 + 0.796)^2 - 4(1.47)(0.796)}\right]$$

$$= 0.319$$

$$A = \frac{1}{Vc}\frac{\alpha - Kpc}{\alpha - \beta} = \frac{1}{13.2}\frac{3.677 - 1.47}{3.677 - 0.319} = 0.0497$$

$$B = \frac{1}{Vc}\frac{\beta - Kpc}{\beta - \alpha} = \frac{1}{13.2}\frac{0.319 - 1.47}{0.319 - 3.677} = 0.0260$$

FIG 23 (con)

$$fC(t) = MIC$$
$$fC(t) - MIC = 0$$

- During infusion: where $0 \leq t \leq T_{inf}$ $$f_{up} \times K_0 \left[ \frac{A}{\alpha} \left( 1 - e^{-\alpha t} + e^{-\alpha \tau} \frac{(1 - e^{\alpha T_{inf}})e^{-\alpha(t-T_{inf})}}{1 - e^{-\alpha \tau}} \right) \right.$$
$$\left. + \frac{B}{\beta} \left( 1 - e^{-\beta t} + e^{-\beta \tau} \frac{(1 - e^{-\beta T_{inf}})e^{-\beta(t-T_{inf})}}{1 - e^{-\beta \tau}} \right) \right] - MIC = 0$$

0.98

$$\times \frac{2000}{3} \left[ \frac{0.0497}{3.677} \left( 1 - e^{-3.677t} + e^{-3.677 \times 8} \frac{(1 - e^{-3.677 \times 3})e^{-3.677(t-3)}}{1 - e^{-3.677 \times 8}} \right) \right.$$
$$\left. + \frac{0.0260}{0.319} \left( 1 - e^{-0.319t} + e^{-0.319 \times 8} \frac{(1 - e^{-0.319 \times 3})e^{-0.319(t-3)}}{1 - e^{-0.319 \times 8}} \right) \right] - 8 = 0$$

- After infusion: where $t \, T_{inf} < t < \tau$ $$f_{up} \times K_0 \left[ \frac{A}{\alpha} \left( \frac{(1 - e^{-\alpha T_{inf}})e^{-\alpha(t-T_{inf})}}{1 - e^{-\alpha \tau}} \right) + \frac{B}{\beta} \left( \frac{(1 - e^{-\beta T_{inf}})e^{-\beta(t-T_{inf})}}{1 - e^{-\beta \tau}} \right) \right] - MIC = 0$$

0.98

$$\times \frac{2000}{3} \left[ \frac{0.0497}{3.677} \left( \frac{(1 - e^{-3.677 \times 3})e^{-3.677(t-3)}}{1 - e^{-3.677 \times 8}} \right) \right.$$
$$\left. + \frac{0.0260}{0.319} \left( \frac{(1 - e^{-0.319 \times 3})e^{-0.319(t-3)}}{1 - e^{-0.319 \times 8}} \right) \right] - 8 = 0$$

- Test for special cases at steady-state
  - See if minimum concentration is greater than the MIC (fCmin > MIC)
    - During infusion, minimum concentration would be at $t = 0$:
      - $fC(t = 0) =$ $$0.98 \times$$
$$\frac{2000}{3} \left[ \frac{0.0497}{3.677} \left( 1 - e^{-3.677(0)} + e^{-3.677 \times 8} \frac{(1 - e^{-3.677 \times 3})e^{-3.677(0-3)}}{1 - e^{-3.677 \times 8}} \right) + \right.$$
$$\left. \frac{0.0260}{0.319} \left( 1 - e^{-0.319(0)} + e^{-0.319 \times 8} \frac{1 - e^{-0.319 \times 3})e^{-0.319(0-3)}}{e^{-0.319 \times 8}} \right) \right]$$

- $fC(t = 0) = 7.247$ mg/L $< 8 \, mg/L$
  - See if maximum concentration is less than the MIC (fCmax $< MIC$)

FIG 23 (con)

- Highest concentration would occur at the time the infusion ends (t = Tinf = 3hr)
  - $fC(t=3)=$ 0.98 x $$\frac{2000}{3}\left[\frac{0.0497}{3.677}\left(1-e^{-3.677(3)}+e^{-3.677X8}\frac{(1-e^{-3.677X3})e^{-3.677(3-3)}}{1-e^{-3.677X8}}\right)+\right.$$
  $$\left.\frac{0.0260}{0.319}\left(1-e^{-0.319(3)}+e^{-0.319X8}\frac{(1-e^{-0.319X3})e^{-0.319(3-3)}}{1-e^{-0.319X8}}\right)\right]$$

- $fC(t=3) = 44.48\ mg/L > 8\ mg/L$

- Since the above conditions have not been met, t1 and t2 can now be calculated:
  - t1 = 0.0163 hr (using algorithm)
  - t2 = 7.69 hr (using algorithm)

Thus, $$\%fT>MIC=\frac{t2-t1}{\tau}x\ 100=\frac{7.69-0.0163}{8}x\ 100=95.9\%$$

SYSTEM AND METHOD FOR RANKING OPTIONS FOR MEDICAL TREATMENTS

CROSS-REFERENCE TO RELATED APPLICATION

This application is a continuation-in-part of U.S. application Ser. No. 14/600,948, entitled "SYSTEM AND METHOD FOR RANKING OPTIONS FOR MEDICAL TREATMENTS," filed Jan. 20, 2015, which is hereby incorporated herein by reference in its entirety for all purposes.

FIELD OF INVENTION

The Invention relates generally to systems and methods for enabling health care providers to discriminate among potential anti-infective therapies for the treatment of selected infectious diseases.

BACKGROUND OF INVENTION

The goal of anti-infective stewardship is to select therapies that optimize the probability of positive outcomes for patients suffering from an infection. The primary focus of anti-infective stewardship is the optimal selection of anti-infective therapy, including dose, dosing interval, and duration. Due to the emergence of anti-infective-resistant pathogens, selecting optimal anti-infective therapy is more complex than at any other time since the advent of penicillin.

SUMMARY OF INVENTION

Shortcomings of the prior art are overcome and additional advantages are provided through the provision of a method for improving communication between a patient and a provider, the method includes: obtaining, by a processor, information identifying an infection; based on the information, generating and displaying, by the one or more processors, a list comprising one or more pathogens consistent with the information; obtaining, by the one or more processors, a first indication designating at least one pathogen from the list comprising one or more pathogens; based on at the obtaining of the least one pathogen, generating, by the one or more processors, a list comprising one or more drug therapies utilized to treat the at least one pathogen; obtaining, descriptive information relating to a patient; based on the one or more drug therapies, selecting a pharmacokinetic model; and applying, by the one or more processors, the pharmacokinetic model and utilizing the information relating to the patient to determine, for each of the one or more drug therapies, a probability of attaining a pharmacokinetic-pharmacodynamic (PK-PD) target associated with efficacy for the patient with the infection.

Shortcomings of the prior art are overcome and additional advantages are provided through the provision of a method for improving communication between a patient and a provider, the method includes: obtaining, by one or more processors, information identifying an infection; based on the information, generating and displaying, by the one or more processors, a list comprising one or more pathogens consistent with the information; obtaining, by the one or more processors, a first indication designating at least one pathogen from the list comprising one or more pathogens; based on at the obtaining of the least one pathogen, generating, by the one or more processors, a list comprising one or more drug therapies utilized to treat the at least one pathogen; obtaining, by the one or more processors, descriptive information relating to a patient, the descriptive information comprising one or more data elements selected from the group consisting of: an infection acquired by the patient, a pathogen isolated from the patient, a creatinine clearance of the patient, a weight of the patient, and a height of the patient; based on the one or more drug therapies, selecting a pharmacokinetic model; applying, by the one or more processors, the pharmacokinetic model and utilizing the information relating to the patient to determine, for each of the one or more drug therapies, a probability of attaining a PK-PD target associated with efficacy for the patient with the infection; automatically generating, by the one or more processors, rankings, for each of the one or more drug therapies, by ordering each probability of attaining the PK-PD target associated with efficacy for the patient with the infection, for each of the one or more drug therapies, for the one or more drug therapies; displaying, by the one or more processors, the rankings, wherein the rankings comprise a ranked list with the probability of attaining a PK-PD target associated with efficacy for the patient with the infection for each of the one or more drug therapies, ranked in order of predicted efficacy; responsive to the displaying, obtaining, by the one or more processors, a third indication comprising designation of a drug therapy from the one or more drug therapies displayed; retaining by the one or more processors, the designation on a memory device; prompting, by the one or more processors, through a user interface, a user to provide data indicating an actual efficacy of the drug therapy as utilized by the patient with the infection at one or more predetermined intervals after obtaining the designation; and obtaining, by the one or more processors, responsive to the prompting, the data indicating the actual efficacy of the drug therapy.

Computer systems, computer program products and methods relating to one or more aspects of the technique are also described and may be claimed herein. Further, services relating to one or more aspects of the technique are also described and may be claimed herein.

Additional features are realized through the techniques of the present invention. Other embodiments and aspects of the invention are described in detail herein and are considered a part of the claimed invention.

BRIEF DESCRIPTION OF DRAWINGS

One or more aspects are particularly pointed out and distinctly claimed as examples in the claims at the conclusion of the specification. The foregoing and objects, features, and advantages of one or more aspects are apparent from the following detailed description taken in conjunction with the accompanying drawings in which:

FIG. 22 depicts a model related to an aspect of an embodiment of the present invention; and FIG. 23 depicts an example of a two compartment model that is utilized when evaluating meropenem.

DETAILED DESCRIPTION OF THE INVENTION

Figure 1:
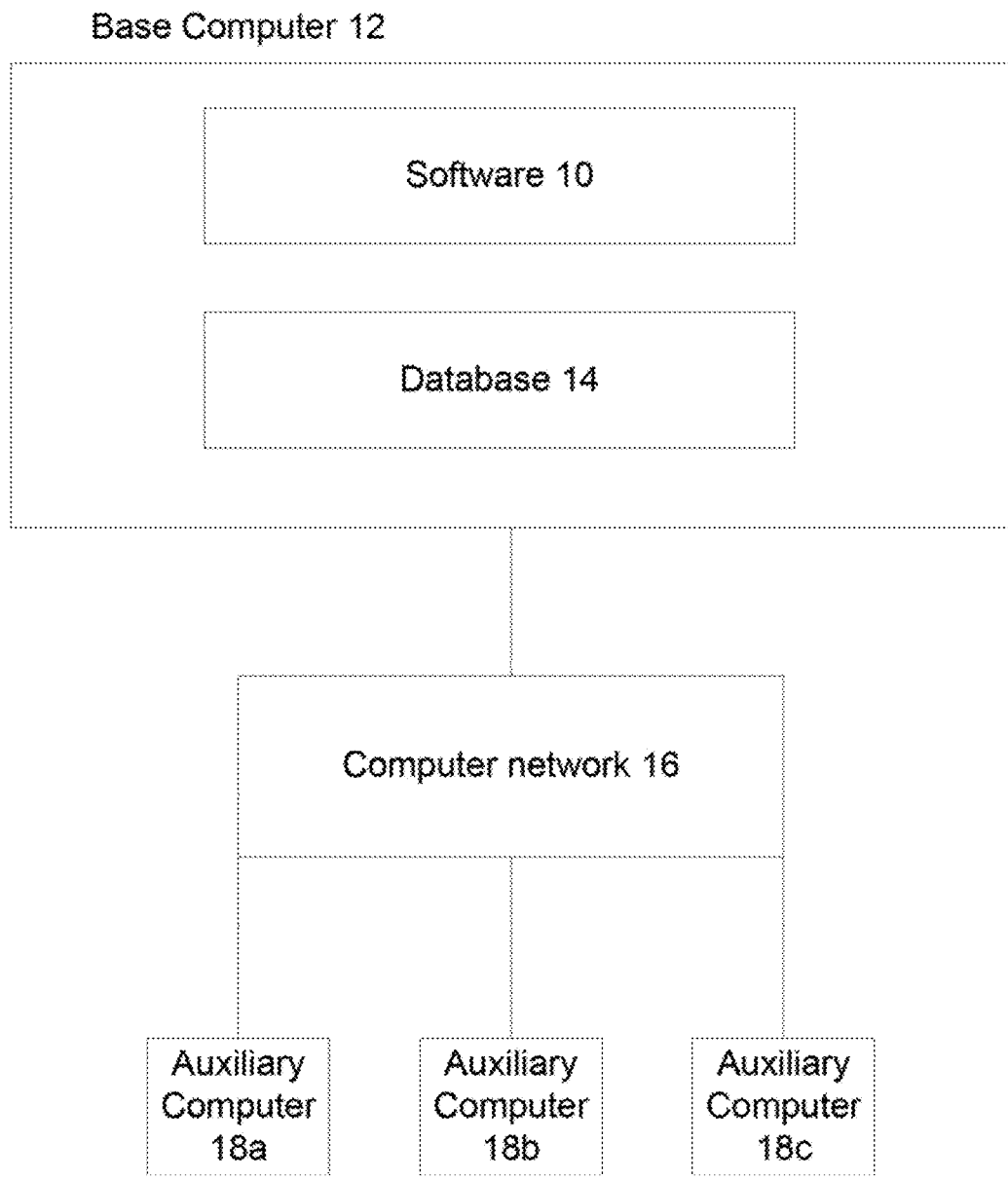
FIG. 1 depicts one example of an aspect of a computing environment used to execute one or more aspects of an embodiment of the present invention.

The accompanying figures, in which like reference numerals refer to identical or functionally similar elements throughout the separate views and which are incorporated in and form a part of the specification, further illustrate the present invention and, together with the detailed description of the invention, serve to explain the principles of the present invention. As understood by one of skill in the art, the accompanying figures are provided for ease of understanding and illustrate aspects of certain embodiments of the present invention. The invention is not limited to the embodiments depicted in the figures.

As understood by one of skill in the art, program code, as referred to throughout this application, includes both software and hardware. For example, program code in certain embodiments of the present invention includes fixed function hardware, while other embodiments utilized a software-based implementation of the functionality described. Certain embodiments combine both types of program code.

Aspects of the present invention and certain features, advantages, and details thereof, are explained more fully below with reference to the non-limiting examples illustrated in the accompanying drawings. Descriptions of well-known materials, fabrication tools, processing techniques, etc., are omitted so as not to unnecessarily obscure the invention in detail. It should be understood, however, that the detailed description and the specific examples, while indicating aspects of the invention, are given by way of illustration only, and not by way of limitation. Various substitutions, modifications, additions, and/or arrangements, within the spirit and/or scope of the underlying inventive concepts will be apparent to those skilled in the art from this disclosure.

Appropriate treatment with anti-infective therapies, including but not limited to, antibiotics, antibacterial, antifungals, antivirals, and/or antimicrobials involves many factors that cannot be controlled by clinicians. For example, factors such as inter-patient variability in drug exposure, the minimum inhibitory concentration (MIC) of the infecting pathogen, and the patient's clinical status, can affect the probability of attaining a PK-PD target associated with efficacy for a drug regimen. The MIC refers to the minimum concentration of a drug therapy that will inhibit the growth of the isolated pathogen. Despite these uncertainties, embodiments of the present method and system enable a clinician (user) to obtain estimates of the probability of attaining PK-PD targets associated with efficacy in the context of predefined factors based upon the selection and application of pharmacokinetic models and simulation by program code executed on at least one processor of a computer system. In order to describe the concentration of drug over time in the body, pharmacokinetic models can be used to describe the disposition of a drug including where and how fast the drug is transferring throughout the body. As discussed below, embodiments of the present invention provide significantly more than existing approaches to providing drug therapy recommendations.

In an embodiment of the present invention, the predefined factors that enable the present technique to estimate probability of attaining a PK-PD target associated with efficacy outcome include, but are not limited to, factors that are within the control of the clinician and/or known to the clinician.

Embodiments of the present invention estimate anti-infective drug exposure for a given patient using data including, but not limited to, infection(s) acquired by the given patient, pathogen(s) isolated from the given patient, and demographic information describing the given patient, including but not limited to, the patient's creatinine clearance, weight, and height. The present invention obtains inputs and identifies and applies relevant pharmacokinetic models and/or tabular outputs to create a listing of potentially useful drug therapies. In embodiments of the present invention, results of the present technique include different options for antibiotic dosing regimens (which consider drug, dose and the dosing interval) for a given patient including drug, dose, and the dosing interval and a comparison of these different options with a ranking based on the probability of attaining PK-PD targets associated with efficacy. An embodiment of the present invention is designed to provide information rather than recommendations for individual patients. The information provided, including but not limited to, the options, may be utilized for decision support and not as a final recommendation without clinical judgment (i.e., without the consideration of other factors such as adverse events).

In an embodiment of the present invention, upon obtaining information related to the given person, for each drug therapy considered, the invention indexes drug exposure to a measure of susceptibility, the MIC, which represents the concentration of drug that inhibits the growth of the pathogen being considered. The MIC can either be a known value, a distribution of values, or the value of defining susceptibility based on in vitro susceptibility test interpretive criteria. In this embodiment, the indexed drug exposure for each drug, which is referred to as a PK-PD index, can take several forms, including but not limited to the following: the ratio of the area under the concentration time-curve over a period of time (e.g., 24 hours) to the MIC (AUC:MIC ratio), the percent of the dosing interval that the drug concentration remains above the MIC (% time above MIC), and the ratio of the maximal drug concentration in the dosing interval to the MIC (Cmax:MIC ratio). The PK-PD index for a given drug and dosing regimen is compared to that required for efficacy, based on pre-clinical or clinical infection exposure-response models. Using one or more equations and/or models that account for sources of variability, the probability of attaining a PK-PD index relative to those associated with efficacy based on pre-clinical or clinical infection exposure-response models (i.e., PK-PD targets associated with efficacy) for each listed antibiotic and dose regimen is then determined for that patient.

In an embodiment of the present invention, the software can determine a ranking for each evaluated drug therapy based on the probability of attaining a PK-PD target associated with efficacy relative to other identified relevant therapies.

In an embodiment of the present invention, collected information and resulting probabilities are stored for future access, for example, in a data store or a database that is accessible to program code executing on a processor in an embodiment of the present invention.

In a further embodiment of the present invention, a user can utilize the software to track results after an option is relayed to a given individual. In an embodiment of the present invention, the program code utilizes the patient information and the relevant data to estimate the probability of attaining a PK-PD target associated with efficacy for a given drug regimen. In order to provide the user with a full view of treatment options, in an embodiment of the present invention, in addition to evaluating the anti-infective used by the program code, the program code also identifies additional anti-infectives for consideration based on the patient information and/or relevant data. The one or more anti-infective obtained by the program code from the user as well as the additional anti-infectives may both be considered by the program code when estimating the probability of attaining a PK-PD target associated with efficacy for a given patient.

In an embodiment of the present invention, program code executing on one or more processors utilizes patient outcome data to train a machine learning data model in order to predict outcomes for new patients based on past outcomes. In embodiments of the present invention, the program code utilizes aggregate patient demographic, clinical, laboratory and outcome data to construct a base model. The base model describes a relationship between patient response and PK-PD target attainment that accounts for patient-specific response modifiers (e.g., previous antibiotic use, age, clearing organ function, etc.). Thus, with each new patient, the program code utilizes (as explained herein) that new patient's data will be used to estimate PK-PD target attainment and its associated the probability. As discussed herein, the program code ranks (orders) the results (positive responses) and provides the results to a user through a graphical user interface. Responsive to obtaining the ranking a user selects a regimen for the patient. The selection of the ranked results can be based on clinical judgment of a care provider. However, patient response to the selected regimen can be monitored. The monitoring by the program code (e.g., of medical records to obtain data, including but not limited patient response, PK-PD target attainment, patient-specific response modifiers) is utilized by the data to modify the base model. Thus, the base model is continuously improved through this machine learning.

Embodiments of the present invention are inextricably linked to computing and comprise a practical application. Regarding being inextricably linked to computing, embodiments of the present invention utilize the immediacy provided by computing and network communications as well as machine learning in order to automatically generate rankings for drug therapies. In embodiments of the present invention, program code determined relevant drug therapies (in accordance with the details described herein) and orders each relevant therapy by probability of attaining the PK-PD target associated with efficacy for a given patient with an infection. These ranking are displayed in order of predicted efficacy. However, the program code continually improves the accuracy of the results through machine learning. Specifically, the program code can machine learn from the displayed results by obtaining a designation of a drug therapy from the therapies displayed, and retaining, the designation on a memory device. The program code can continue to obtain information related to a patient being treated with the drug therapy (patient response, PK-PD target attainment, patient-specific response modifiers) and utilize this data to train the model. The program code retains this data in the memory device (e.g., one or more memory devices). Thus the program code can continue to automatically provide results to users, with improved efficacy. This machine learning, for example, is inextricably linked to computing. However, the immediacy of the data analyses and calculation and display of results is likewise inextricably linked to computing because the management of the data and coherence and immediacy of the response is enabled through computing technology. Additionally, embodiments of the present invention provide a practical application at least because the program code provides practical results, rankings for different regimens for a given patient, with increasing accuracy. Embodiments of the present invention are additionally not abstract based on the particularity of data elements utilized as well as the tangible results generated by the program code. For example, in some embodiments of the present invention the program code obtains descriptive information that includes data elements, including but not (always) limited to, an infection acquired by the patient, a pathogen isolated from the patient, a creatinine clearance of the patient, a weight of the patient, and a height of the patient. This data is utilized by the program code, in embodiments of the present invention, to automatically generate and provide the aforementioned results.

Embodiments of the present invention comprise a practical application for a number of reasons, some of which are discussed above. However, as another example, program code in some embodiments of the present invention, executing on one or more processors, applies a pharmacokinetic model and utilizes information relating to a patient to determine, for various (determined to be relevant) drug therapies, a probability of attaining a PK-PD target associated with efficacy for the patient with the infection. The program code also automatically generates rankings, for each of the drug therapies, by ordering each probability of attaining the PK-PD target associated with efficacy for the patient with the infection, for each of the drug therapies. The program code also displays the rankings, which comprise a ranked list with the probability of attaining a PK-PD target associated with efficacy for the patient with the infection for each of the drug therapies, ranked in order of predicted efficacy. The program code then obtains a designation of a drug therapy from the drug therapies displayed and retains the designation on a memory device. These aspects are all practical applications.

FIG. 1 is a computer system 100 configured to perform at least one aspect of an embodiment of the present invention. In the embodiment of FIG. 1, software 10 is executed by at least one processor on a computer, termed a base computer 12 in FIG. 1 for clarity. The terms software, program code, computer program code, code, computer program product, and executable instructions, are used interchangeably throughout this application.

The software comprises code that is accessible to the processor and executable by at least one processor of the computer 12. The software can be stored on a memory on the physical computer 12, and/or in a memory and/or on removable media accessible to the computer 12 via a network connection, including but not limited to, a wireless and/or wireless network, utilizing a protocol known to one of skill in the art. The computer may also be configured to act as a web server, which may be capable of running the software and hosting and/or interacting with the database 14. Additionally, the computer can be one or more resources of a cloud computing system, executing the software performing the method described herein, which is accessible to a user as a service. In some of these embodiments of the present invention, any personally identifiable information can be stored locally or not utilized, in order to assuage any security concerns. However, by storing certain of the data in the cloud that does not cannot be used to personally identify patients, the data stored can be utilized by the program code for machine learning and to train the base model utilized to generate ranked options for users.

The base computer 12, as well as any other computer described in the present specification can includes personal computers, servers, smart phones, mobile devices, laptops, desktops, and/or any means of personal or corporate computing device capable of executing the software 10 or portions of the software 10, or communicating with a computer executing the software 10 over a wireless or hard wired network.

In the embodiment of FIG. 1, the base computer is connected to a computer network 16, including but not limited to private and publicly accessible wired and wireless networks, and the Internet. In this embodiment, one or more computers, termed auxiliary computers 18a-18c are communicatively connected to the computer 12 via a computer network 16, including but not limited to, the Internet. The auxiliary computer 18a-18c receive data from the computer 12, via, for example, the web application server on the computer 12 and the auxiliary computers 18a-18c can render (for viewing) determinations regarding the probability of attaining a PK-PD target associated with efficacy for various antibiotics for the treatment of given patients based on data describing the given patient obtained at the base computer 12 and/or stored on the database 14 accessible to a processing resource on the base computer 12, including but not limited to, demographic information, and/or clinical laboratory data. The base computer can obtain data from the auxiliary computers 18a-18c, including but not limited to, the aforementioned descriptive data regarding the given patient for whom an antibiotic option is sought. As understood by one of skill in the art, the program code in various embodiment of the present invention can be stored on a memory resource and/or executed on one or more of the base computer 12 and/or the auxiliary computers 18a-18c.

The base computer 12 in the embodiment of FIG. 1 includes a database 14. Additional embodiments of the present invention utilize databases and other memory devices in different physical locations that are remotely accessible to the base computer 12 executing the software 10. In the embodiment of FIG. 1, the database 14 stores data including, but not limited to, population pharmacokinetic model-based equations and/or tabular outputs for a listing of potentially useful antibiotics that can be used to treat selected infectious diseases, information relating to various antibiotics and patients to whom they were offered by the present method, and/or the results of options returned by embodiments of the present invention.

Figure 2:
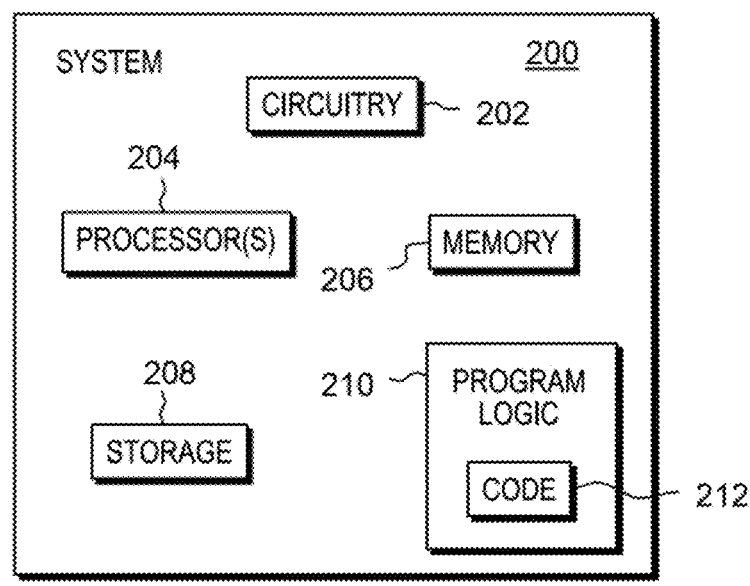
FIG. 2 depicts one embodiment of a single processor computing environment to incorporate and use one or more aspects of the present invention.

FIG. 2 illustrates a block diagram of a resource 200, like base computer 12 and/or auxiliary computers 18a-18c, in computer system 100, which is part of the technical architecture of certain embodiments of the technique. The resource 200 may include a circuitry 202 that may in certain embodiments include a microprocessor 204. The computer system 200 may also include a memory 206 (e.g., a volatile memory device), and storage 208. The storage 208 may include a non-volatile memory device (e.g., EEPROM, ROM, PROM, RAM, DRAM, SRAM, flash, firmware, programmable logic, etc.), magnetic disk drive, optical disk drive, tape drive, etc. The storage 208 may comprise an internal storage device, an attached storage device and/or a network accessible storage device. The system 200 may include a program logic 210 including code 212 that may be loaded into the memory 206 and executed by the microprocessor 204 or circuitry 202.

In certain embodiments, the program logic 210 including code 212 may be stored in the storage 208, or memory 206. In certain other embodiments, the program logic 210 may be implemented in the circuitry 202. Therefore, while FIG. 2 shows the program logic 210 separately from the other elements, the program logic 210 may be implemented in the memory 206 and/or the circuitry 202.

Using the processing resources of a resource 200 to execute software, computer-readable code or instructions, does not limit where this code can be stored. The terms program logic, code, and software are used interchangeably throughout this application.

Figure 3:
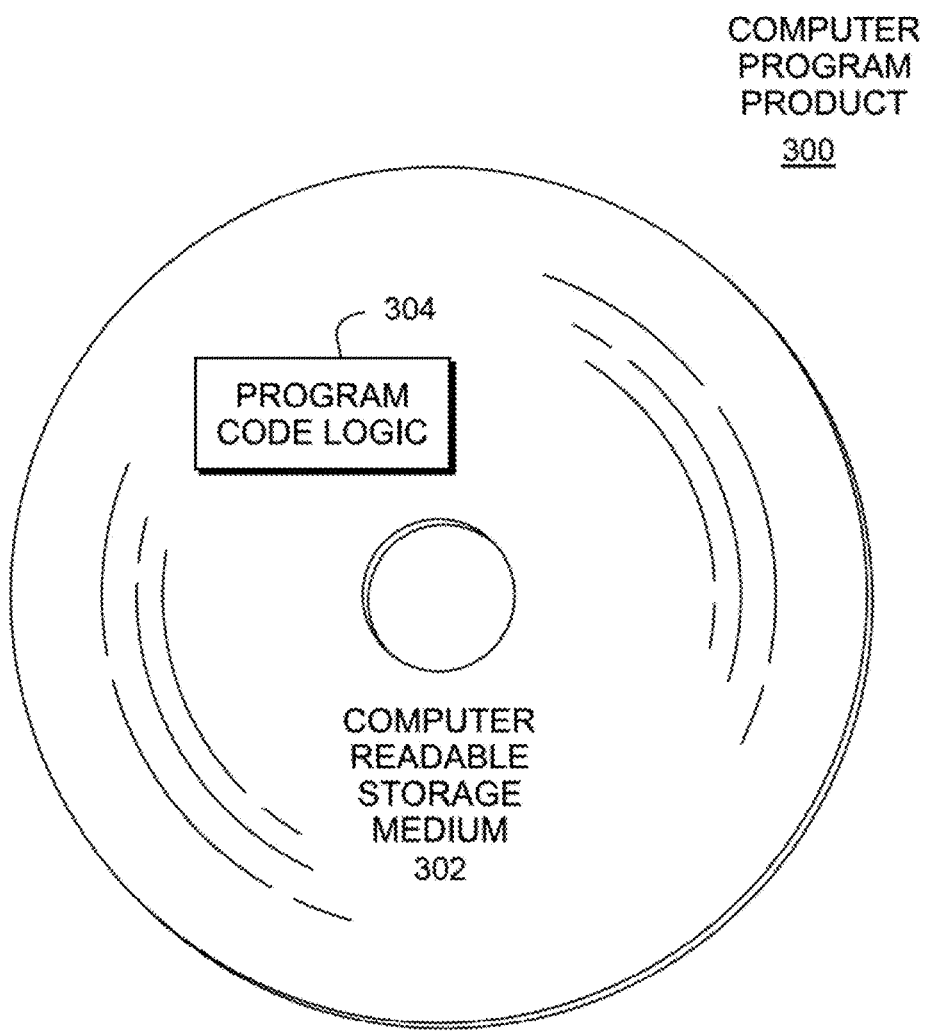
FIG. 3 depicts one embodiment of a computer program product incorporating one or more aspects of the present invention.

Referring to FIG. 3, in one example, a computer program product 300 includes, for instance, one or more non-transitory computer readable storage media 302 to store computer readable program code means or logic 304 thereon to provide and facilitate one or more aspects of the technique.

As will be appreciated by one skilled in the art, aspects of the technique may be embodied as a system, method or computer program product. Accordingly, aspects of the technique may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the technique may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable signal medium may include a propagated data signal with computer readable program code embodied therein, for example, in baseband or as part of a carrier wave. Such a propagated signal may take any of a variety of forms, including, but not limited to, electro-magnetic, optical or any suitable combination thereof. A computer readable signal medium may be any computer readable medium that is not a computer readable storage medium and that can communicate, propagate, or transport a program for use by or in connection with an instruction execution system, apparatus or device.

A computer readable storage medium may be, for example, but not limited to, an electronic, magnetic, optical, electromagnetic, infrared or semiconductor system, apparatus, or device, or any suitable combination of the foregoing. More specific examples (a non-exhaustive list) of the computer readable storage medium include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain or store a program for use by or in connection with an instruction execution system, apparatus, or device.

Program code embodied on a computer readable medium may be transmitted using an appropriate medium, including but not limited to wireless, wireline, optical fiber cable, RF, etc., or any suitable combination of the foregoing.

Computer program code for carrying out operations for aspects of the technique may be written in any combination of one or more programming languages, including an object oriented programming language, such as Java, Smalltalk, C++ or the like, and conventional procedural programming languages, such as the "C" programming language, assembler or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the technique are described herein with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions, also referred to as computer program code, may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the figures illustrate the architecture, functionality, and operation of possible implementations of systems, methods and computer program products according to various embodiments of the technique. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

In addition to the above, one or more aspects of the technique may be provided, offered, deployed, managed, serviced, etc. by a service provider who offers management of customer environments. For instance, the service provider can create, maintain, support, etc. computer code and/or a computer infrastructure that performs one or more aspects of the technique for one or more customers. In return, the service provider may receive payment from the customer under a subscription and/or fee agreement, as examples. Additionally or alternatively, the service provider may receive payment from the sale of advertising content to one or more third parties.

In one aspect of the technique, an application may be deployed for performing one or more aspects of the technique. As one example, the deploying of an application comprises providing computer infrastructure operable to perform one or more aspects of the technique.

As a further aspect of the technique, a computing infrastructure may be deployed comprising integrating computer readable code into a computing system, in which the code in combination with the computing system is capable of performing one or more aspects of the technique. As a further aspect of the technique, the system can operate in a peer to peer mode where certain system resources, including but not limited to, one or more databases, is/are shared, but the program code executable by one or more processors is loaded locally on each computer (workstation).

As yet a further aspect of the technique, a process for integrating computing infrastructure comprising integrating computer readable code into a computer system may be provided. The computer system comprises a computer readable medium, in which the computer medium comprises one or more aspects of the technique. The code in combination with the computer system is capable of performing one or more aspects of the technique.

Further, other types of computing environments can benefit from one or more aspects of the technique. As an example, an environment may include an emulator (e.g., software or other emulation mechanisms), in which a particular architecture (including, for instance, instruction execution, architected functions, such as address translation, and architected registers) or a subset thereof is emulated (e.g., on a native computer system having a processor and memory). In such an environment, one or more emulation functions of the emulator can implement one or more aspects of the technique, even though a computer executing the emulator may have a different architecture than the capabilities being emulated. As one example, in emulation mode, the specific instruction or operation being emulated is decoded, and an appropriate emulation function is built to implement the individual instruction or operation.

In an emulation environment, a host computer includes, for instance, a memory to store instructions and data; an instruction fetch unit to fetch instructions from memory and to optionally, provide local buffering for the fetched instruction; an instruction decode unit to receive the fetched instructions and to determine the type of instructions that have been fetched; and an instruction execution unit to execute the instructions. Execution may include loading data into a register from memory; storing data back to memory from a register; or performing some type of arithmetic or logical operation, as determined by the decode unit. In one example, each unit is implemented in software. For instance, the operations being performed by the units are implemented as one or more subroutines within emulator software.

Further, a data processing system suitable for storing and/or executing program code is usable that includes at least one processor coupled directly or indirectly to memory elements through a system bus. The memory elements include, for instance, local memory employed during actual execution of the program code, bulk storage, and cache memory which provide temporary storage of at least some program code in order to reduce the number of times code must be retrieved from bulk storage during execution.

Input/Output or I/O devices (including, but not limited to, keyboards, displays, pointing devices, DASD, tape, CDs, DVDs, thumb drives and other memory media, etc.) can be coupled to the system either directly or through intervening I/O controllers. Network adapters may also be coupled to the system to enable the data processing system to become coupled to other data processing systems or remote printers or storage devices through intervening private or public networks. Modems, cable modems, and Ethernet cards are just a few of the available types of network adapters.

Figure 4:
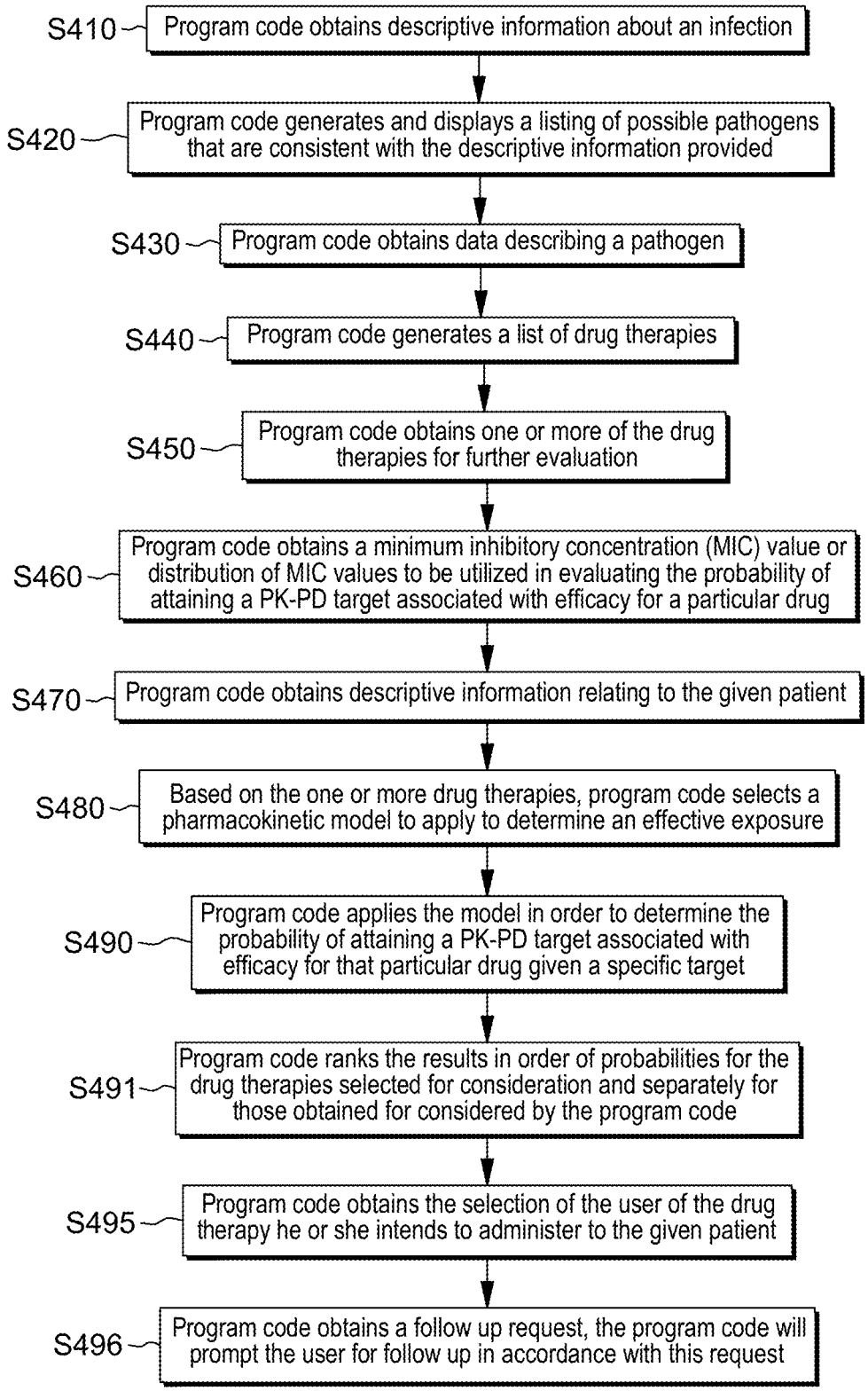
FIG. 4 depicts a workflow of an embodiment of the present invention.

FIG. 4 depicts a workflow 400 of aspects of an embodiment of the present technique. In order to estimate the anti-infective drug exposure for a given patient, program code executed by at least one processor on a computer resource, such as resource 200, obtains descriptive information about an infection (S410), including but not limited to, where the infection is located, and/or where the infection was acquired.

Figure 5:
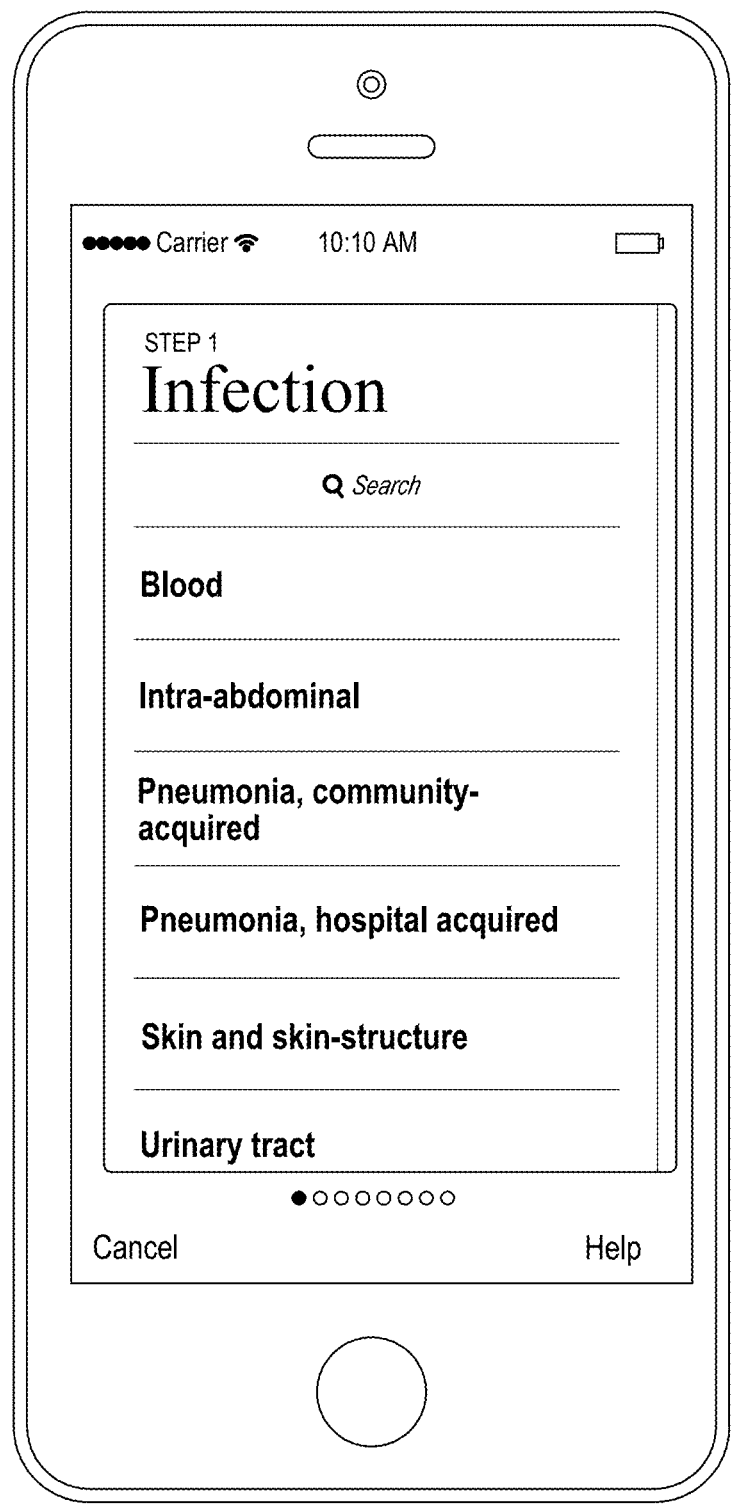
FIG. 5-20 depict examples of an exemplary graphical user interface (GUI) produced by an aspect of the present invention.

FIG. 5 depicts an example of a graphical user interface 510 on a mobile device 500, which is a computer resource that can be an aspect of embodiments of the present invention. The screen depicted in FIG. 5 is termed the "Infection" screen where a user, for example, a clinician, can select descriptive terms to assist the program code in executing on a processor of this computer resource in obtaining further characteristics about the infection.

Figure 6:
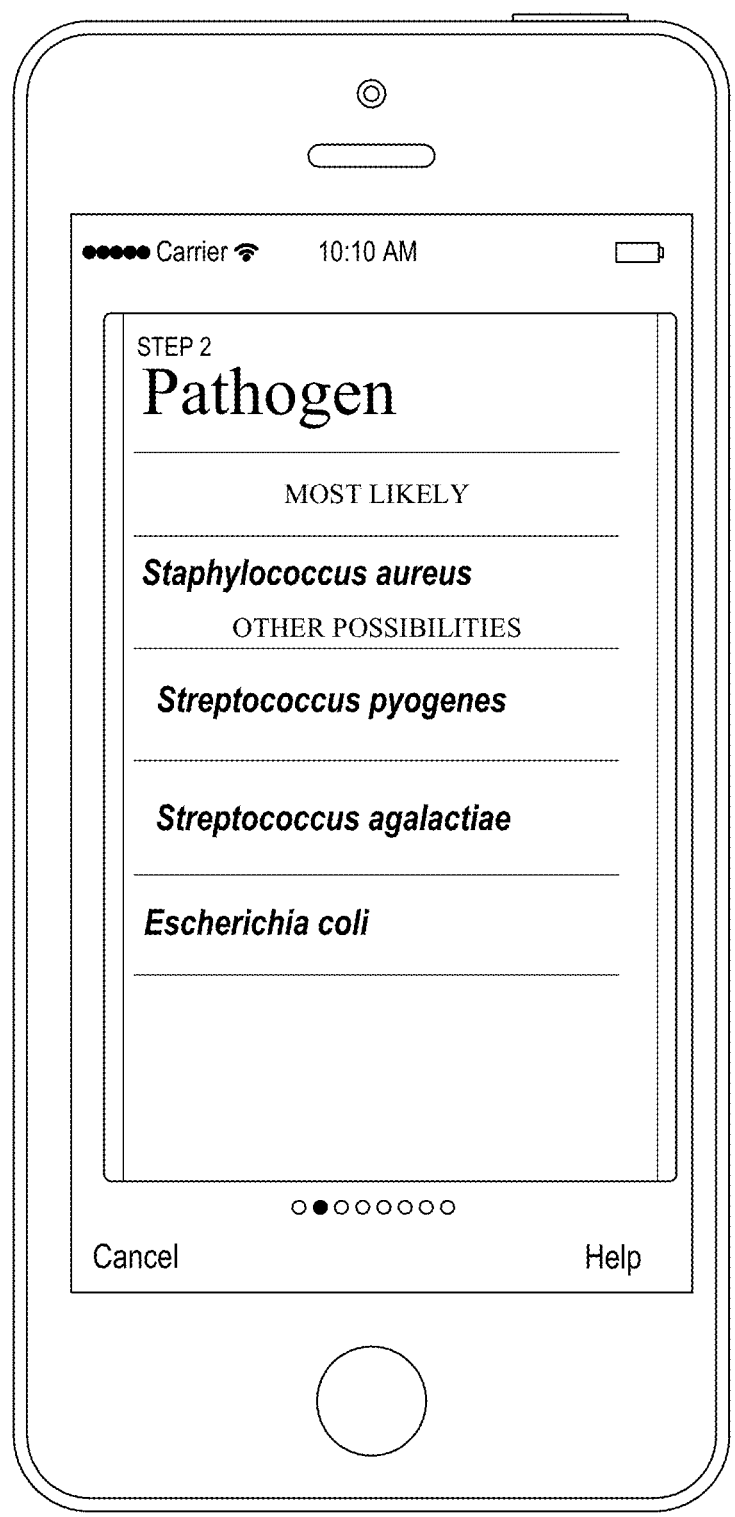

Returning to FIG. 4, upon obtaining descriptive information about the infection, the program code generates and displays a listing of possible pathogens that are consistent with the descriptive information provided (S420). As seen to FIG. 6, which depicts a GUI with an exemplary screen listing possible pathogens, the listing generated by the program code can include an indication of what is the most likely and/or possible pathogen, based on the description. In an embodiment of the present invention, the program code executed by the processor can make this determination by accessing data on a storage medium that is located either local to the computer resource or accessible via a communications connection.

Figure 7:
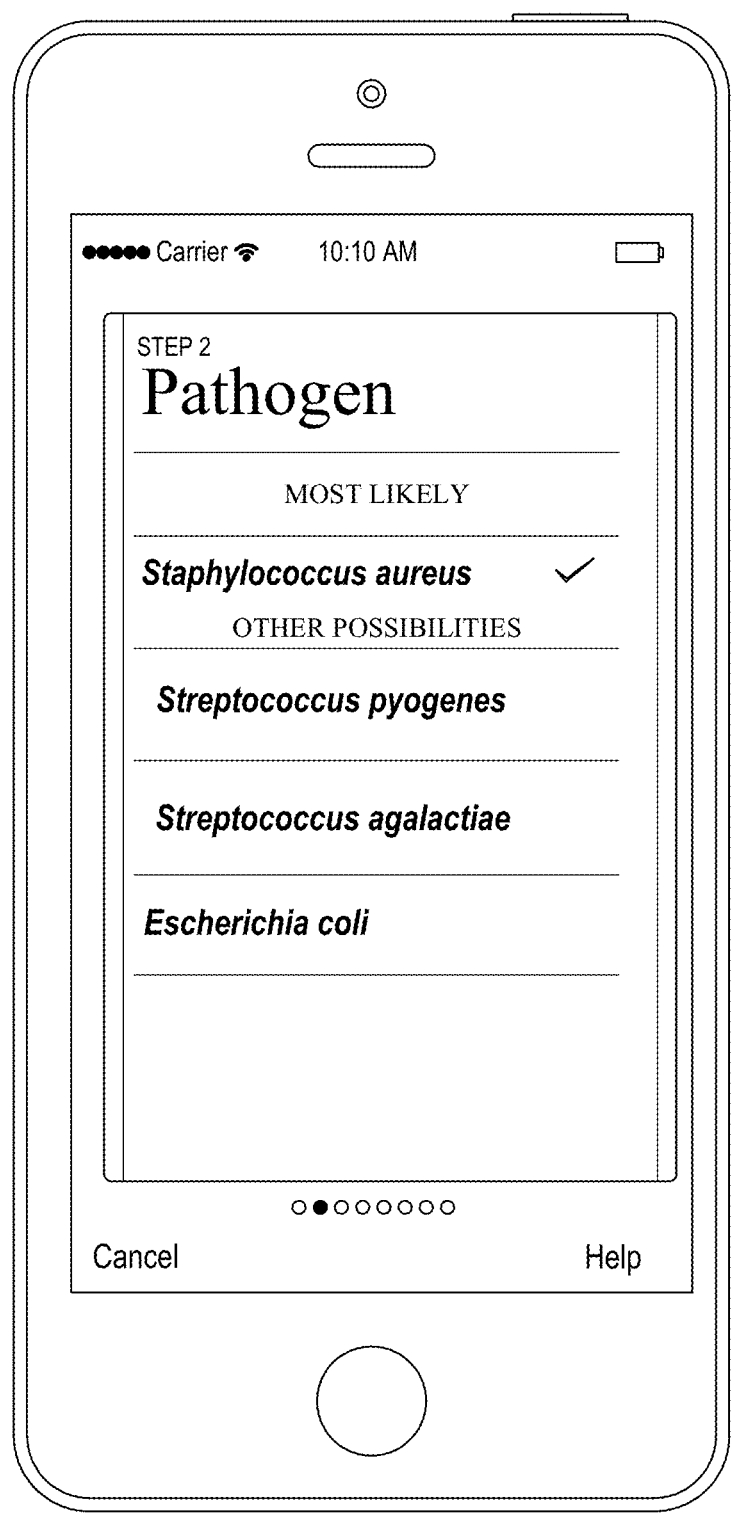

Returning to FIG. 4, the program code executed by a processor of the computer resource obtains data describing a pathogen (S430). As seen in FIG. 7, a user of this embodiment of the present invention, the program code can obtain the pathogen when the user makes a selection in the GUI that is displayed by the program code listing possible pathogens.

Responsive to receiving the data describing a pathogen, the program code executed by a processor generates a list of drug therapies (S440), including but not limited to, antibiotics, that are options for treating the pathogen. The list generated by the program code executed by a processor can include a single result or a group of results, based upon the information obtained.

In an embodiment of the present invention, data related to drug therapies that may comprise the list created by the program code can be stored on a memory resource that is integral to the computer resource and/or accessible to the computer resource via a communications connection.

Figure 8:
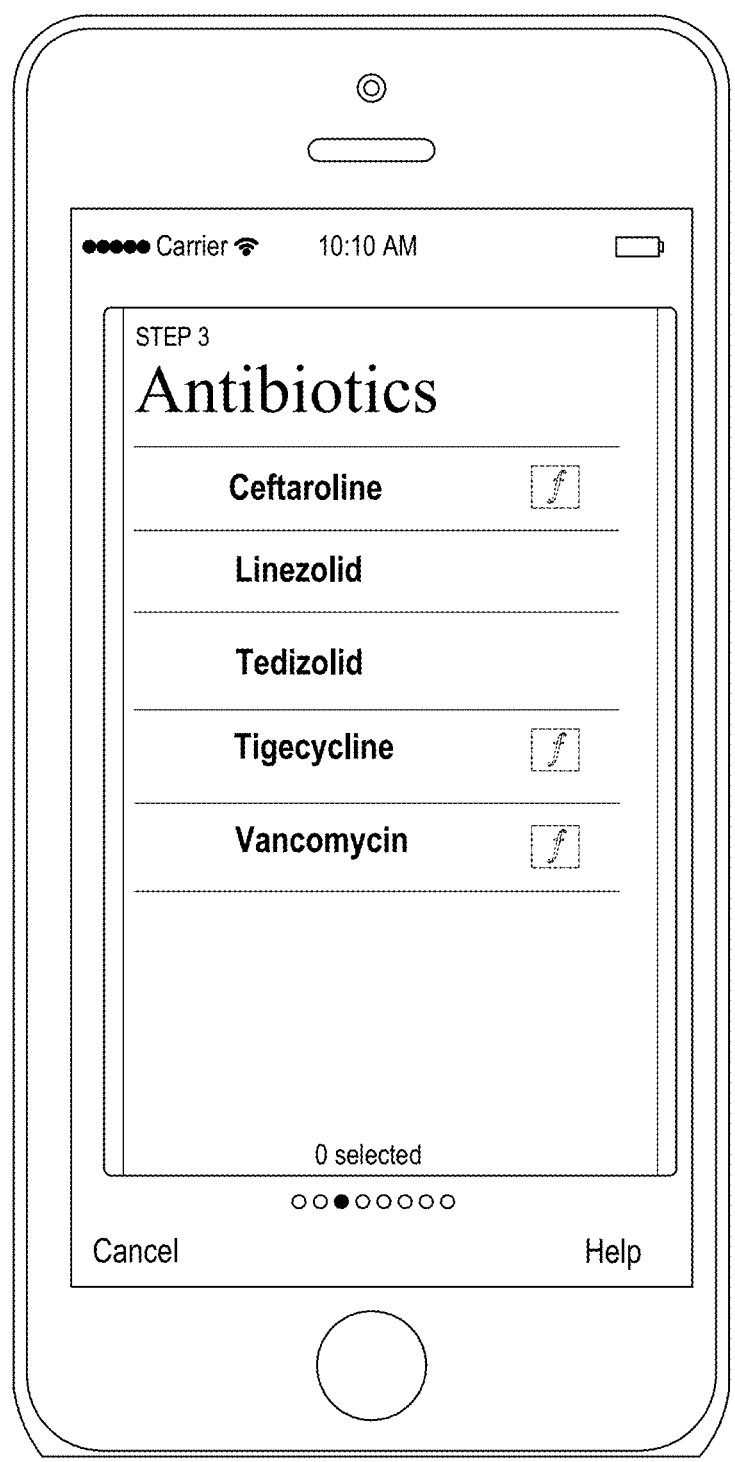

FIG. 8 is an example of a list of drug therapies generated by program code in an embodiment of the present invention. In the example of FIG. 8, a list of antibiotics was generated by the program code and displayed to the user. From this list of drug therapies related to the identified pathogen and/or infection, in an embodiment of the present invention, the user, such as a clinician, can select from the list one or more drug therapies for further evaluation in order to receive the probability of attaining the PK-PD target associated with efficacy for the drug in treating a given patient. In an embodiment of the present invention, the drug therapies that are listed to a user by the program code comprise drug therapies that have known success in treating the pathogen obtained by the program code, e.g., identified by the user through an input into the computer resource.

Figure 9:
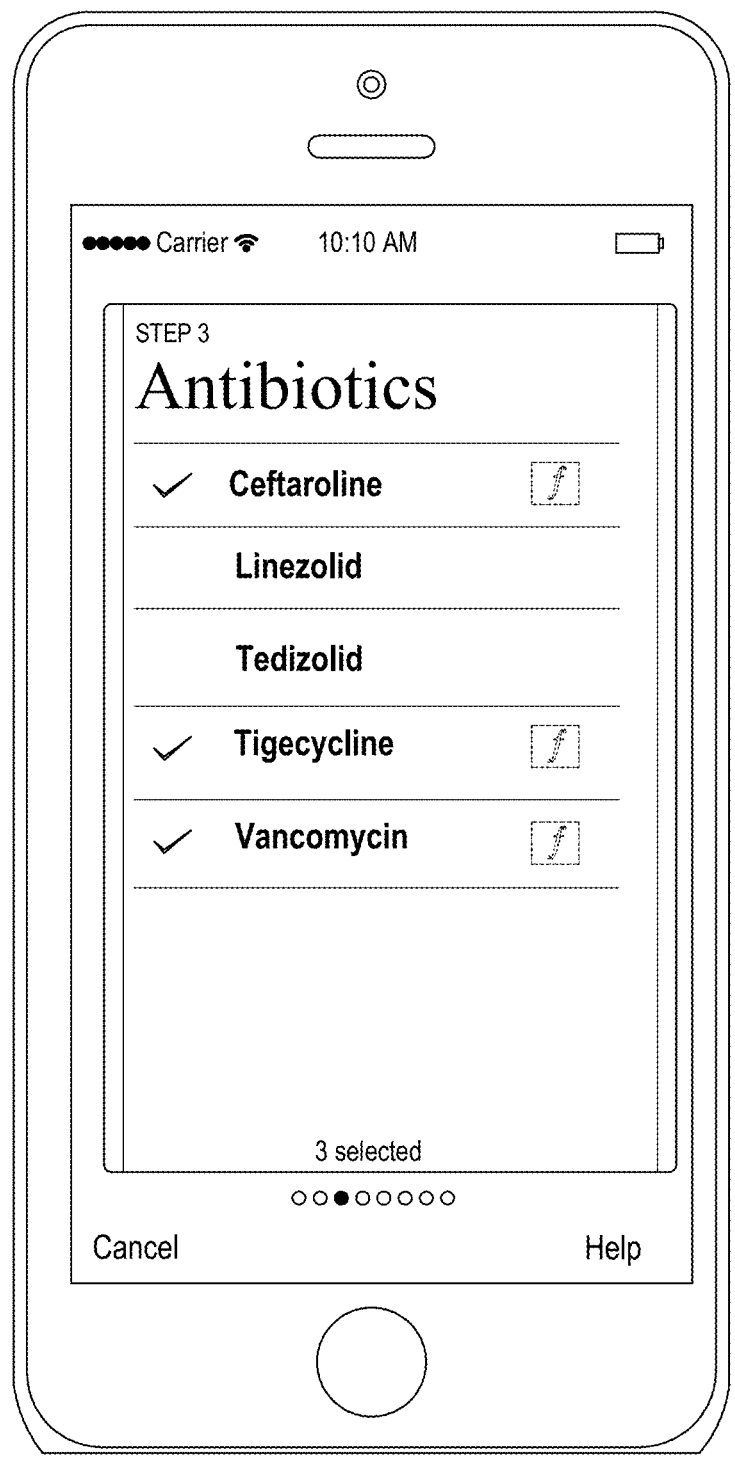

Returning to FIG. 4, the program code obtains one or more of the drug therapies for further evaluation by the program code (S450). As aforementioned, the program code can receive the one or more drug therapies for further evaluation based upon a selection made by the user using an input device, such as a touch screen. FIG. 9 in an example of a screen of a GUI, in an embodiment of the present invention, where a user has selected drug therapies, in this example, antibiotics, for further analysis by the program code. In an embodiment of the present invention, in addition to the program code listing drug therapies from which a user can select, a user can also enter one or more drug therapies for evaluation. The program code may retain the entered drug therapies and save the drug therapies and their relationship in treating a given pathogen, on a memory resource, for future use, including but not limited to one or more remote memory resource(s). In an embodiment of the present invention, the program code obtains a listing of potentially useful antibiotics that can be used to treat selected infectious diseases indicated by the infections and/or pathogens experienced by the given patient from a memory resource.

In a further embodiment of the present invention, the program code evaluates all the drug therapies provided rather than enable a user, or an automatic process, to limit the number of therapies further evaluated.

Returning to FIG. 4, the program code also obtains a minimum inhibitory concentration (MIC) value or distribution of MIC values to be utilized in evaluating the probability of attaining a PK-PD target associated with efficacy for a particular drug (S460). The user can select the type of MIC distribution that the program code will apply The MIC is the lowest concentration of an antimicrobial that will inhibit the visible growth of a microorganism after overnight incubation. Because the MIC value relates to an in vitro measurement of the efficacy of a drug, the efficacy of the drug therapy, as related to a given patient, is not immediately apparent without utilizing additional parameters and applying a relevant pharmacokinetic model, which is discussed later.

Figure 10:
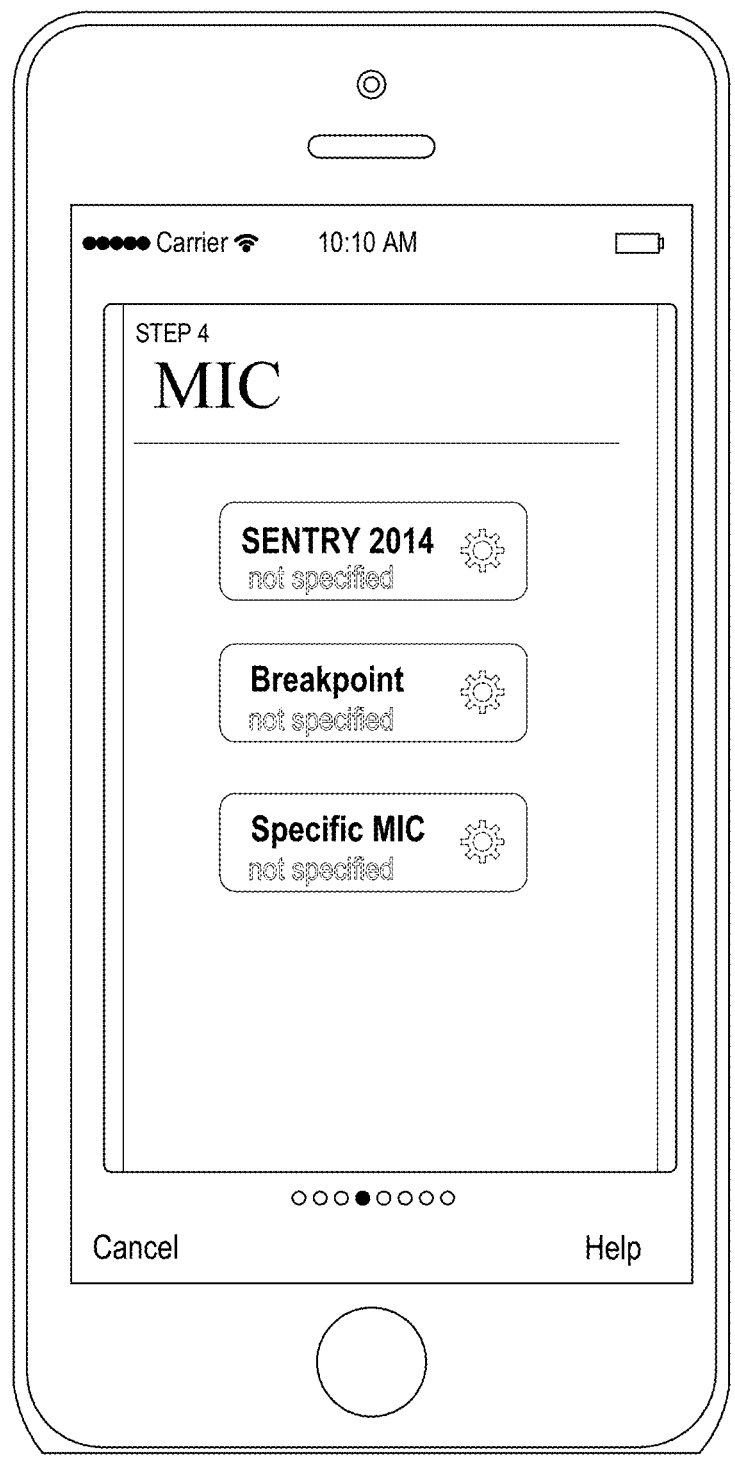
Figure 11:
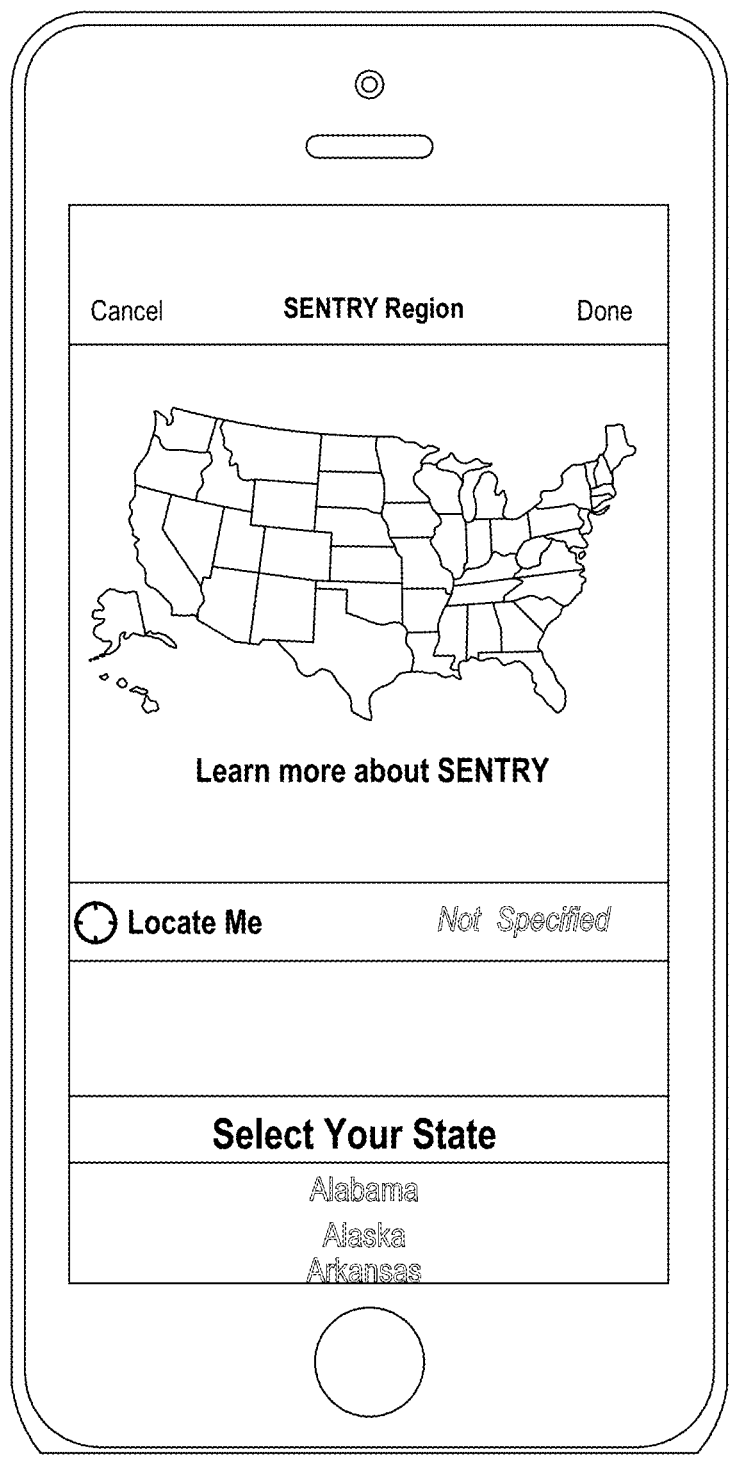

Depending upon the type of drug therapies being contemplated, the user may select a MIC distribution rather than a fixed MIC value. FIG. 10 is an example of a GUI utilized in an embodiment of the present invention to display to a user select choices of MIC values. As susceptibility patterns and hence, likely MIC values may be influenced by the geographical location of a given patient, should a user select a distribution of MIC values based on surveillance data, including but not limited to, the SENTRY repository of data, such as SENTRY 2014), the user can be prompted to enter the location of the patient, as seen in FIG. 11.

In an embodiment of the present invention, the computer resource can include a GPS that the program code utilizes to find the location of the user and therefore, apply the relevant MIC distribution. As seen in FIG. 11, the program code displays a "Locate me" function. In this example, when a user selects this location function, the program code will request location information from the GPS and receive this information, which it will use to generate a user location, responsive to the request.

Returning to FIG. 4, as discussed earlier, demographic information related to the patient is also utilized by the program code determining the probability of attaining PK-PD targets associated with efficacy for known drug therapies. Thus, the program code obtains descriptive information relating to the given patient (S470). The descriptive information includes, but is not limited to, the weight of the patient and the creatinine clearance of the given patient.

Figure 12:
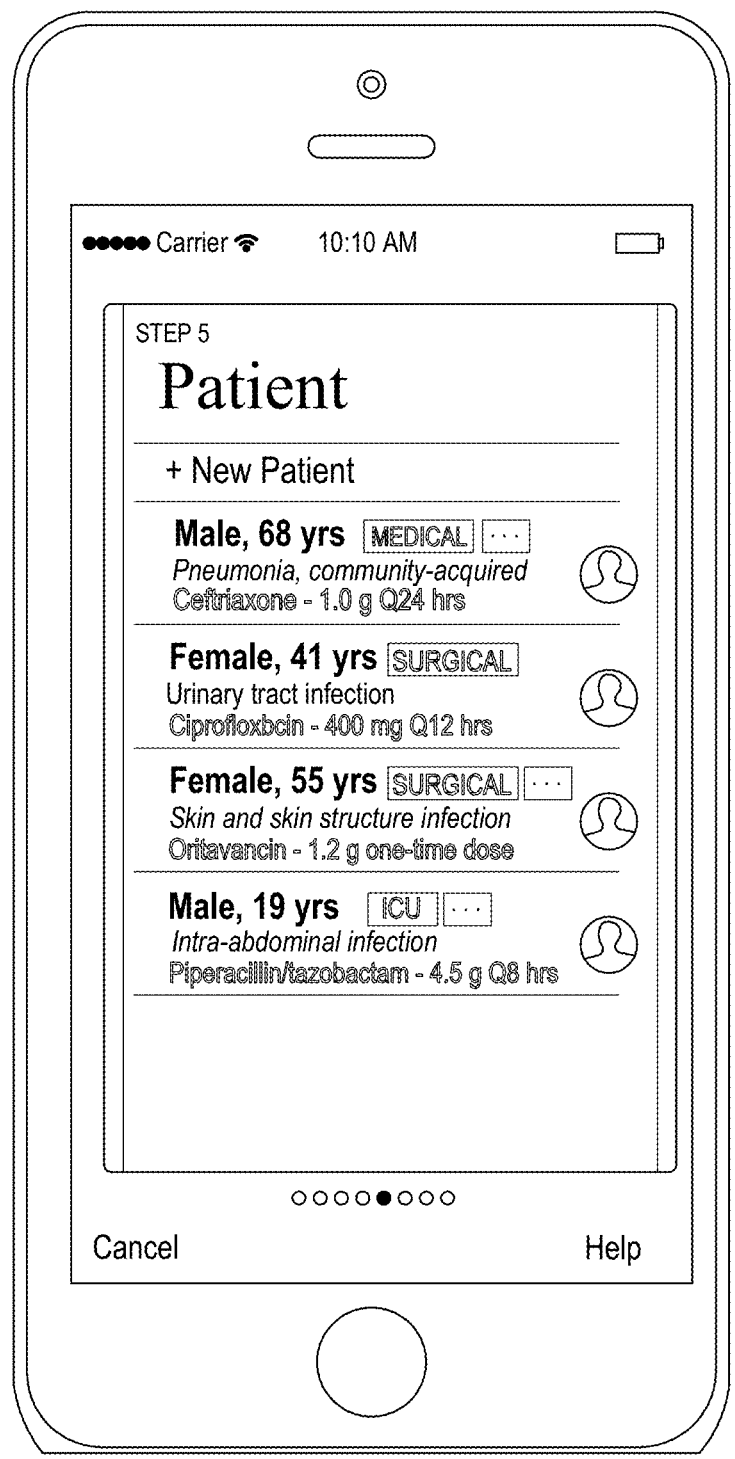

In an embodiment of the present invention, the program code displays a list of descriptive information relating to existing patients, enabling the user to select a patient from this listing. The existing patient records may be retained on an accessible memory resource, such as a database. An example of a GUI where the program code renders a list of existing patients is displayed as FIG. 12.

Figure 13A:
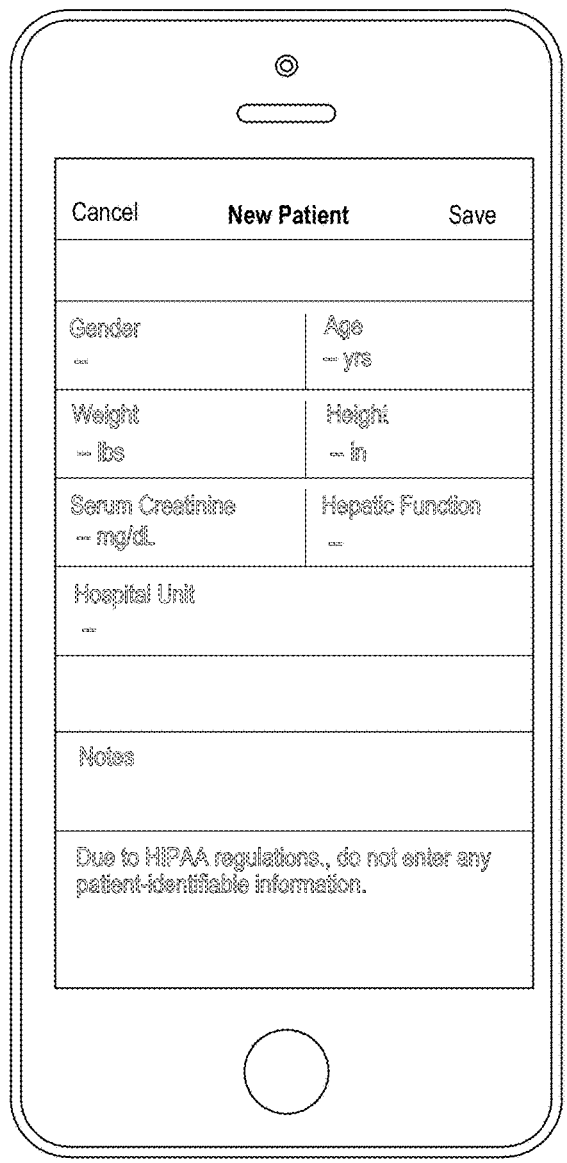
Figure 13B:
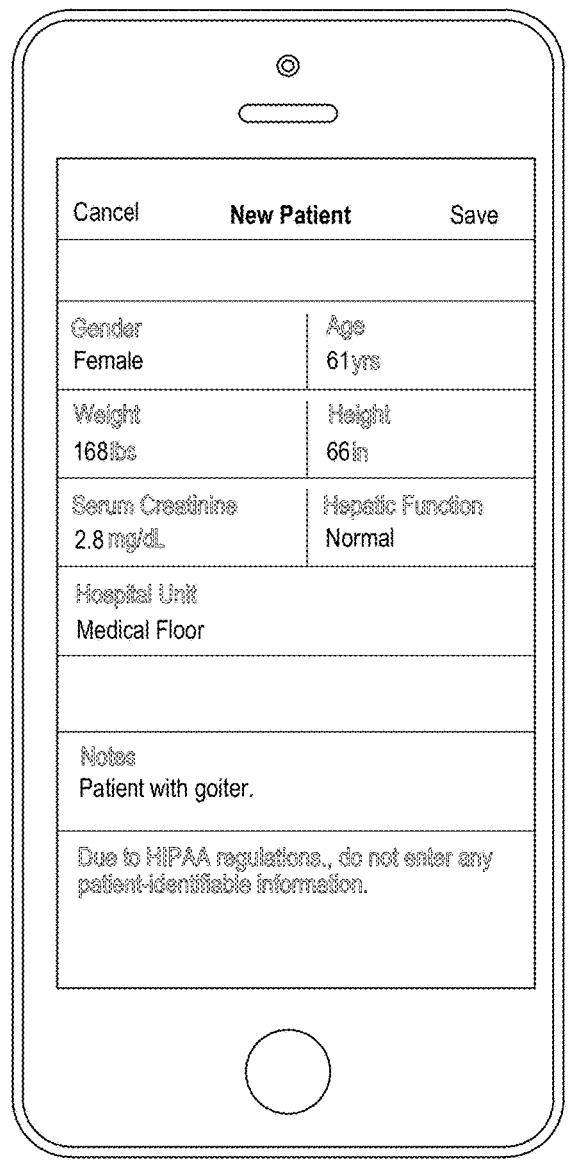

In an embodiment of the present invention, program code executed by a processor can obtain user information from user entry. For example, a user can enter patient information related to a new patient. This option is also visible in FIG. 12 and if selected, in an embodiment of the present invention, the program code produces a GUI where the user can enter new patient information, as seen in FIGS. 13A and 13B. As aforementioned, among the parameters requested in the GUI and therefore, received by the program code, are the patient's weight and serum creatinine. As seen in FIGS. 13A and 13B, in compliance with HIPAA regulations, the GUI where a user can enter patient information can be configured to warn a user not to enter any patient-identifiable information. Additionally, in an embodiment of the present invention, the program code does not obtain and/or retain private information in violation of HIPAA.

Figure 14:
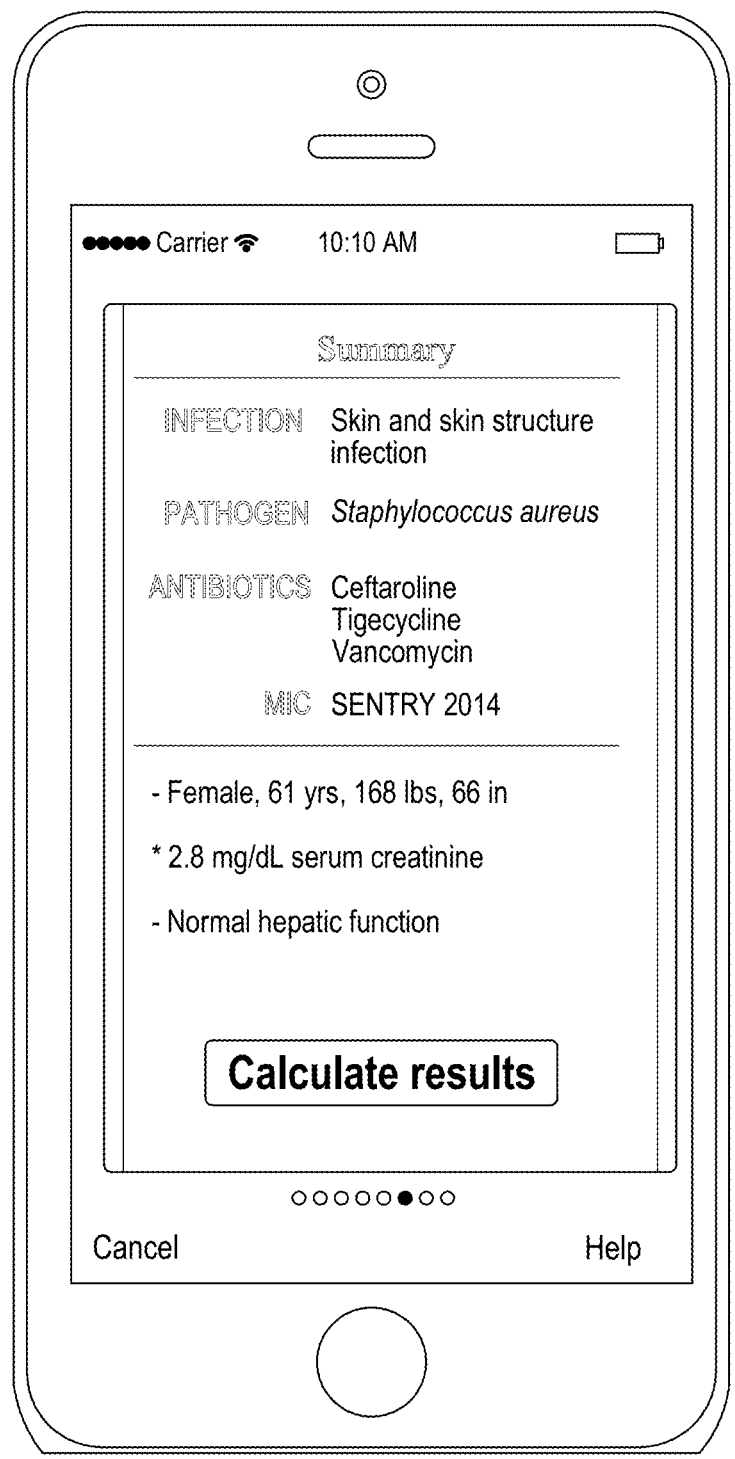

Once the program code has obtained the drug therapy being considered, including descriptive factors that may include, but are not limited to, the dosage, duration of infusion, and/or dosing interval, the MIC or the MIC distribution, and the aforementioned patient characteristics, the program code determines the probability of attaining the PK-PD target associated with efficacy for the selected drug therapy and/or therapies. In an embodiment of the present invention, the program code executed by a processor displays a summary screen to a user that includes the data obtained that the program code will utilize to determine PK-PD target attainment. FIG. 14 is an example of a summary screen.

Referring to FIG. 14, the summary screen lists the infection, the pathogen, the selected drug therapies, which, in this example, are antibiotics, and the selection made for MIC. The summary screen also lists descriptive information about the patient, in this example, the gender, age, weight, height, serum creatinine, and category of hepatic function. The program code will vary the parameters utilized in determining the probability of attaining a PK-PD target associated with efficacy for each therapy, based upon that therapy. For example, while the height of the patient may assist in a determination for a given drug therapy, that parameter may not be used by the program code in determining the probability of attaining a PK-PD target associated with efficacy for a different drug. Thus, returning to FIG. 4, based upon each drug therapy selected, the program code selects a pharmacokinetic model to apply to determine an exposure and the probability of attaining a PK-PD target associated with efficacy for that drug therapy, which in an embodiment of the present invention, is expressed as a percent probability (S480). The program code utilizes at least one pharmacokinetic model in determining the probability of attaining a PK-PD target associated with efficacy for a given drug therapy for a given patient. Thus, upon selecting a pharmacokinetic model, the program code applies the model in order to determine the probability of attaining a PK-PD target associated with efficacy for that particular drug given a specific target (S490).

The pharmacokinetic models associated with different drug therapies use mathematical representations of parts of the body to describe the time-course of drug concentrations in the body. To describe the parts of the body affecting the time-course of drug concentrations, the body of the patient can be understood as containing compartments. The models account for n number of compartments. Some models utilize three compartments. Taking the drug therapy, meropenem as an example, its pharmacokinetics can be described using two compartments. The two compartments represent blood and tissue. This two compartment type of pharmacokinetic model is applied during and after infusion.

In a two-compartment pharmacokinetic model discussed later in this document, Vc stands for "volume of the central compartment" which is usually blood. Thus, when a drug is infused (Ko), it will be input into this compartment. The second compartment, Vp, stands for "peripheral compartment" which approximates the tissue. The transfer rate of drug between these two compartments is called "distributional clearance" (CLd). In the central compartment, drug will be eliminated (by routes such as renal excretion or metabolism) and this is considered an output and is termed "total clearance" (CLt). These parameters can be calculated if equations are known for a given drug therapy, and, as aforementioned, for most drug therapies, the patient weight, and creatinine clearance for a given patient are also known.

Returning to FIG. 14, when utilizing the GUI of an embodiment of the present invention, the user can visually verify that the information on the summary screen is correct and submit this information to the program code for determination of the probability of attaining a PK-PD target associated with efficacy for each selected drug therapy, as discussed in reference to FIG. 4.

Figure 15:
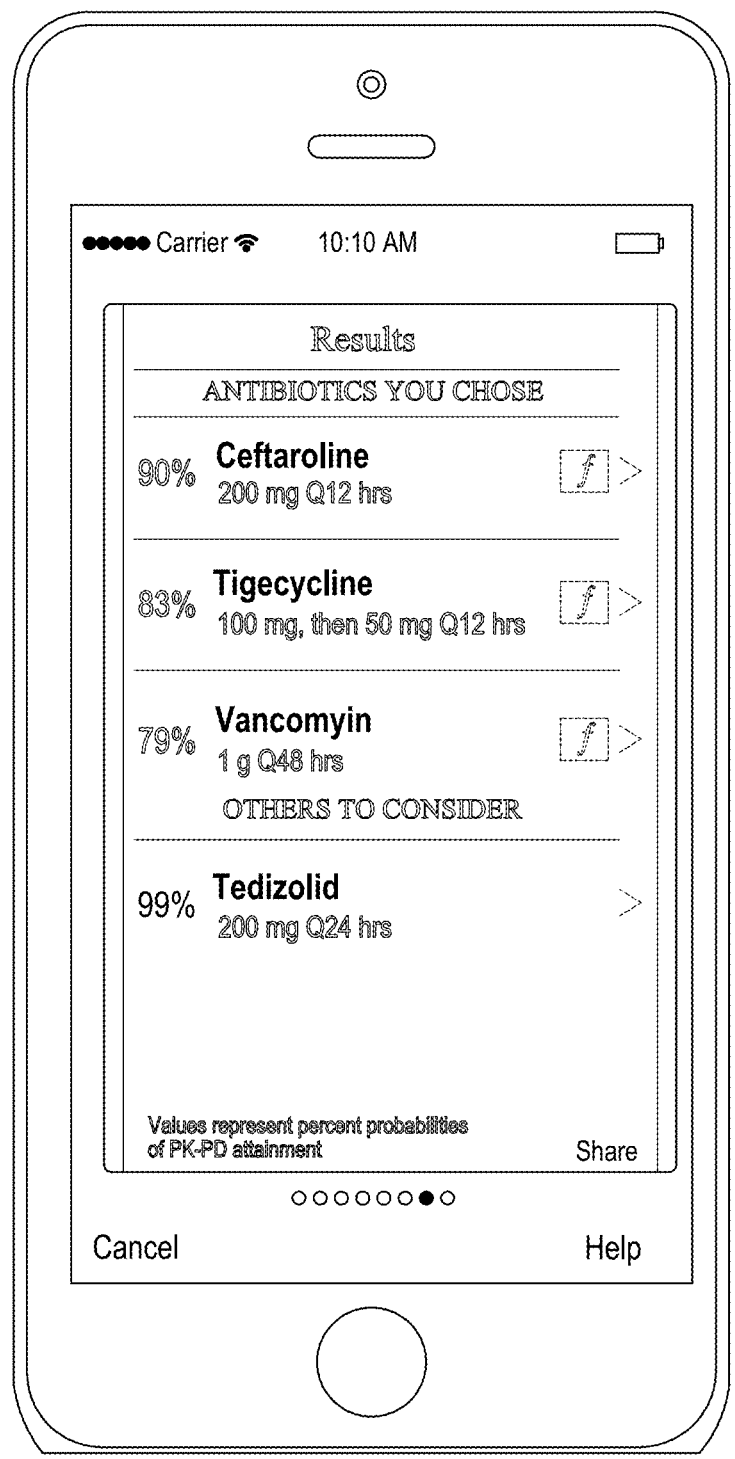

In an embodiment of the present invention, once the program code has determined a probability of attaining a PK-PD target associated with efficacy for each selected drug therapy and/or drug therapies that were not selected by the user, the program code ranks the results in order of probabilities for the drug therapies selected for consideration and separately for those obtained for considered by the program code (S491). FIG. 15 is an example of a screen of a GUI utilized in an embodiment of the present invention to display the determined probabilities of PK-PD target attainment, and rank the drug therapies by these probabilities.

Figure 16:
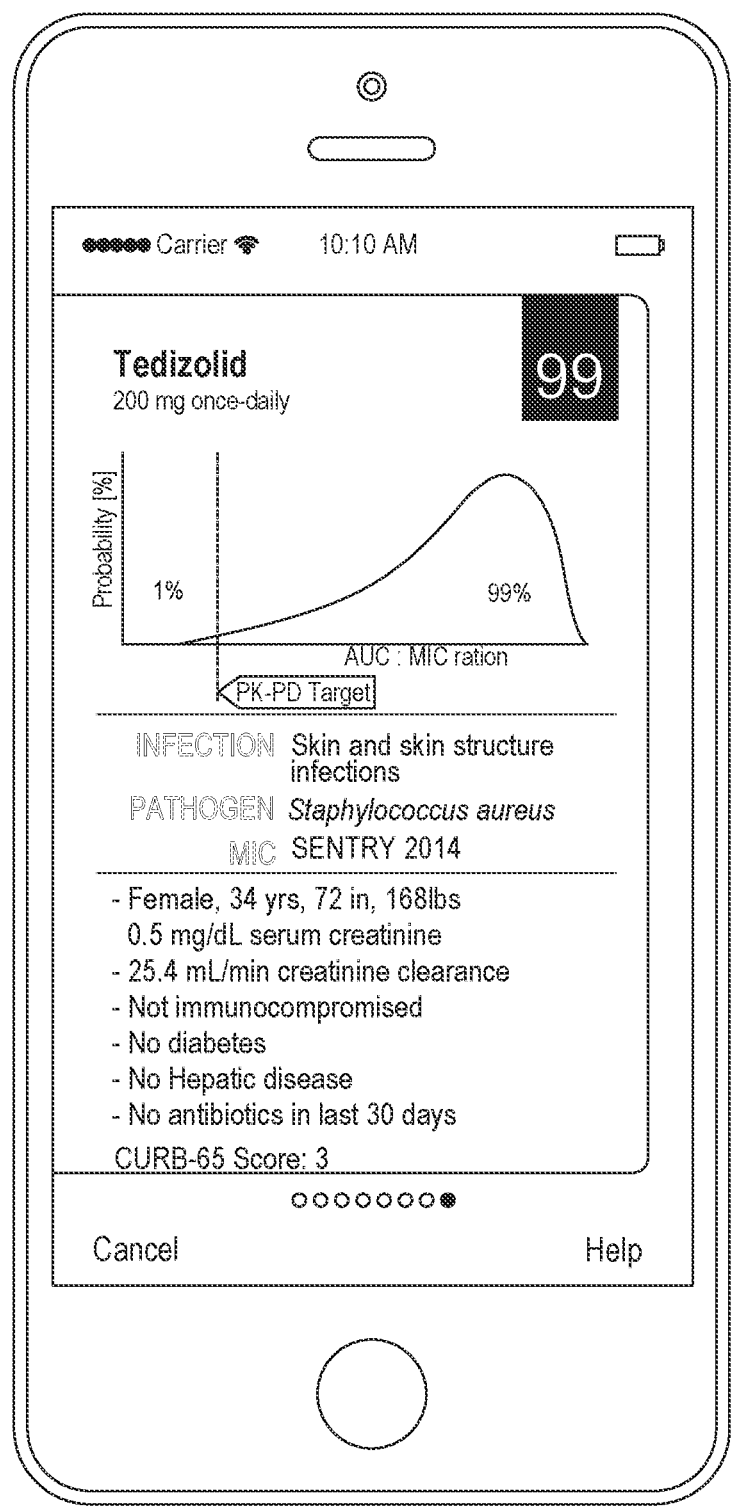

After providing a user with the probability of attaining a PK-PD target associated with efficacy for drug therapies considered, in an embodiment of the present invention, the program code can obtain the selection of the user of the drug therapy he or she intends to administer to the given patient (S495). In an embodiment of the present invention, the program code retains the selection on a memory device accessible to the processor. In an embodiment of the present invention, the program code can generate a GUI that displays individual results for the probability of attaining a PK-PD target associated with efficacy for various drug therapies from a listing screen, such as FIG. 15. FIG. 16 is an example of this type of detail screen, in this case, for the drug therapy Tedizolid. The probability of attaining the PK-PD target associated with efficacy for the drug therapy is presented in the context of the infection and/or pathogen obtained by the program code upon entry of information by a user.

Figure 17:
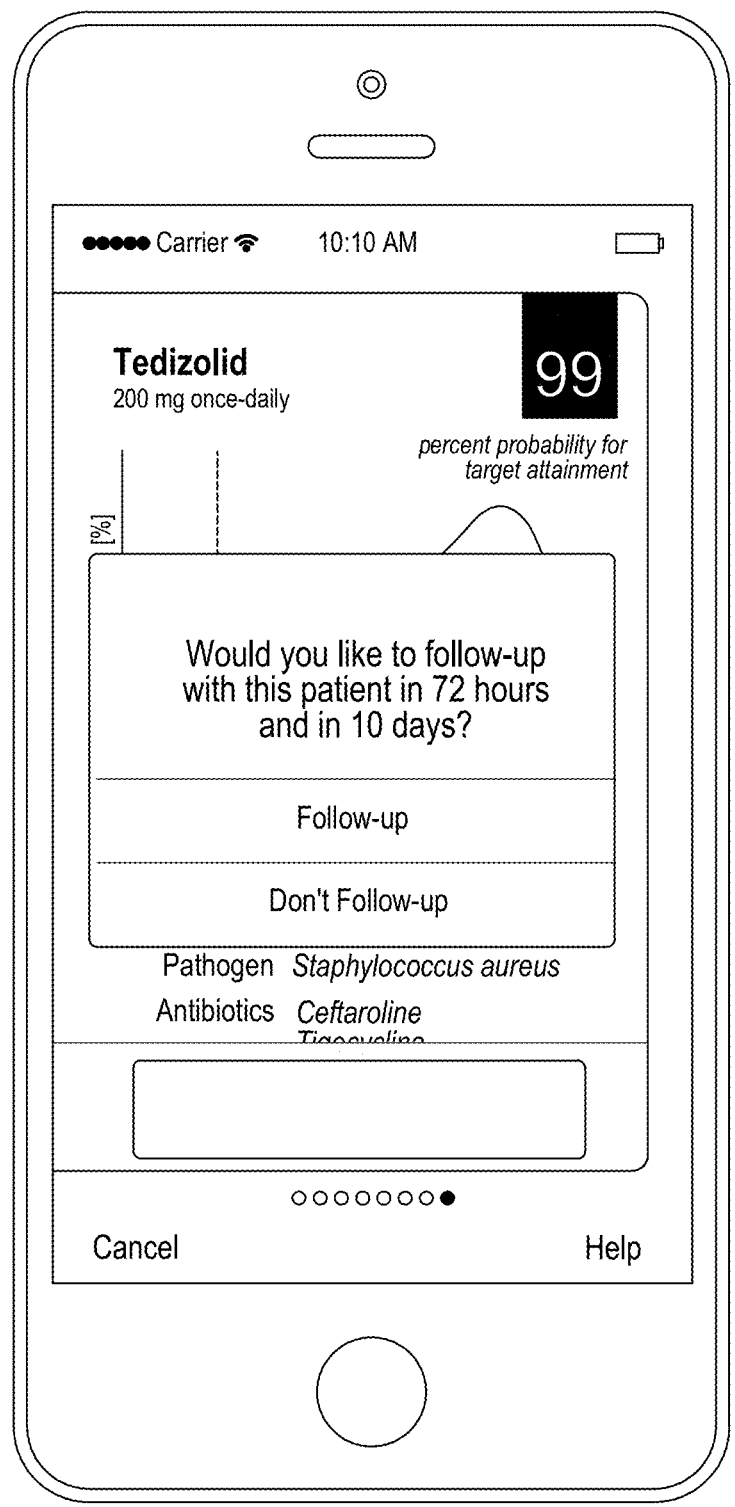
Figure 18:
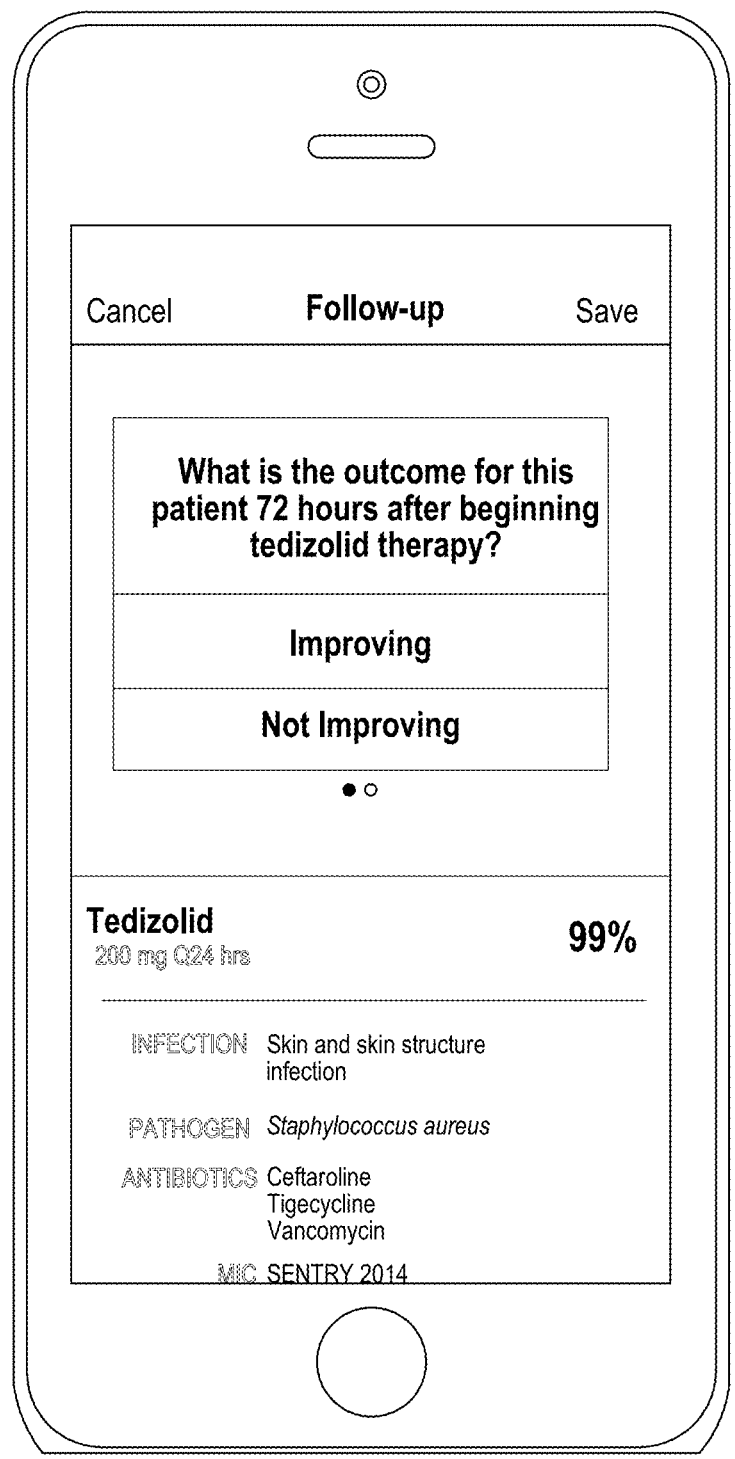

In an embodiment of the present invention, the user can track the actual efficacy of the drug therapy selected, for example, to compare and contrast the expected outcome with the actual outcome. In FIG. 17, once the user has selected the drug therapy from the drug therapies returned as options, the user can select whether he or she would like to be prompted to follow up with the patient. Should the user opt to follow up, in an embodiment of the present invention, the program code will display a reminder to the user to follow up regarding a given patient. FIG. 18 is an example of a possible display for this follow up activity and additionally may collect information regarding efficacy, including but not limited to, requesting that a user enter information and/or importing information from an external data repository. In an embodiment of the present invention, the reminder generated by the program code can be audible and/or visual.

Returning to FIG. 4, in an embodiment of the present invention where the program code obtains a follow up request, the program code will prompt the user for follow up in accordance with this request (S496).

Figure 19:
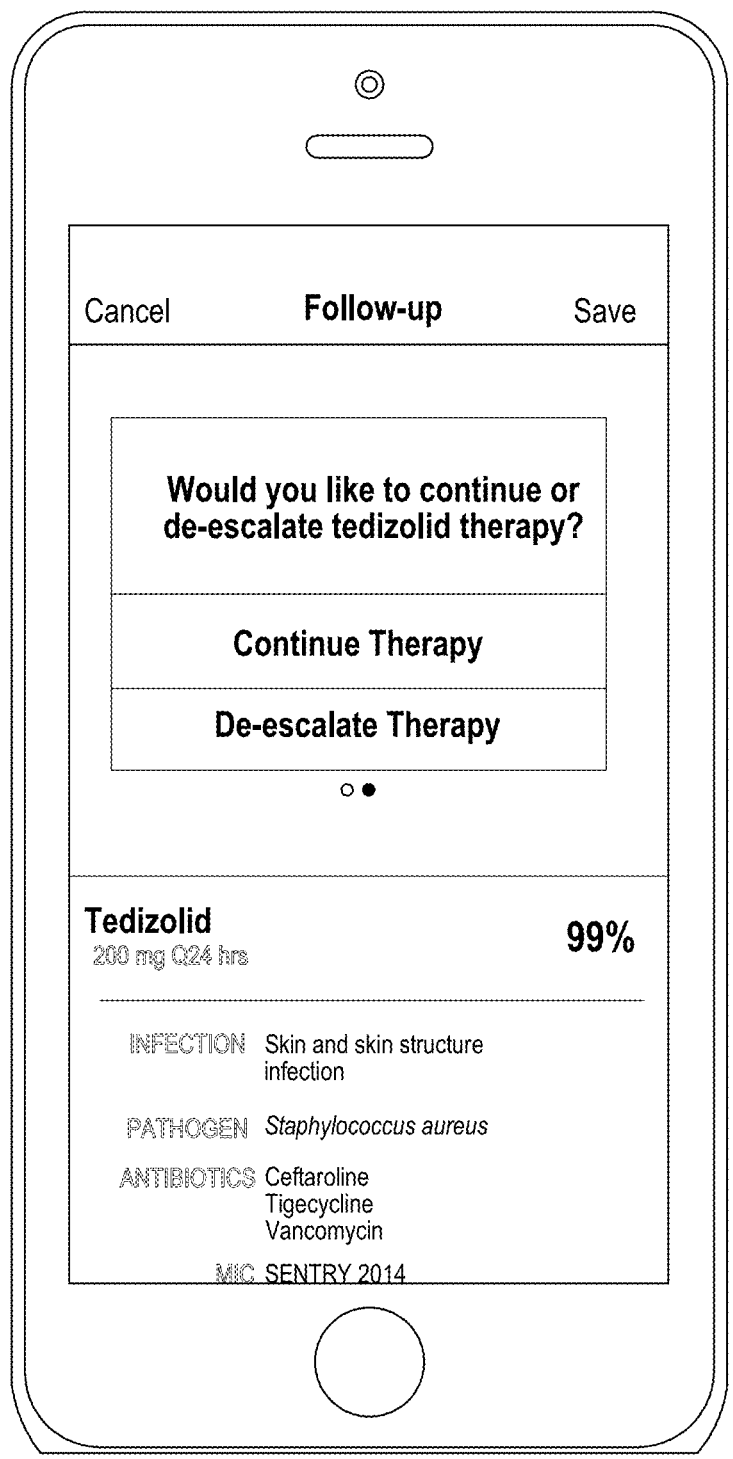
Figure 20:
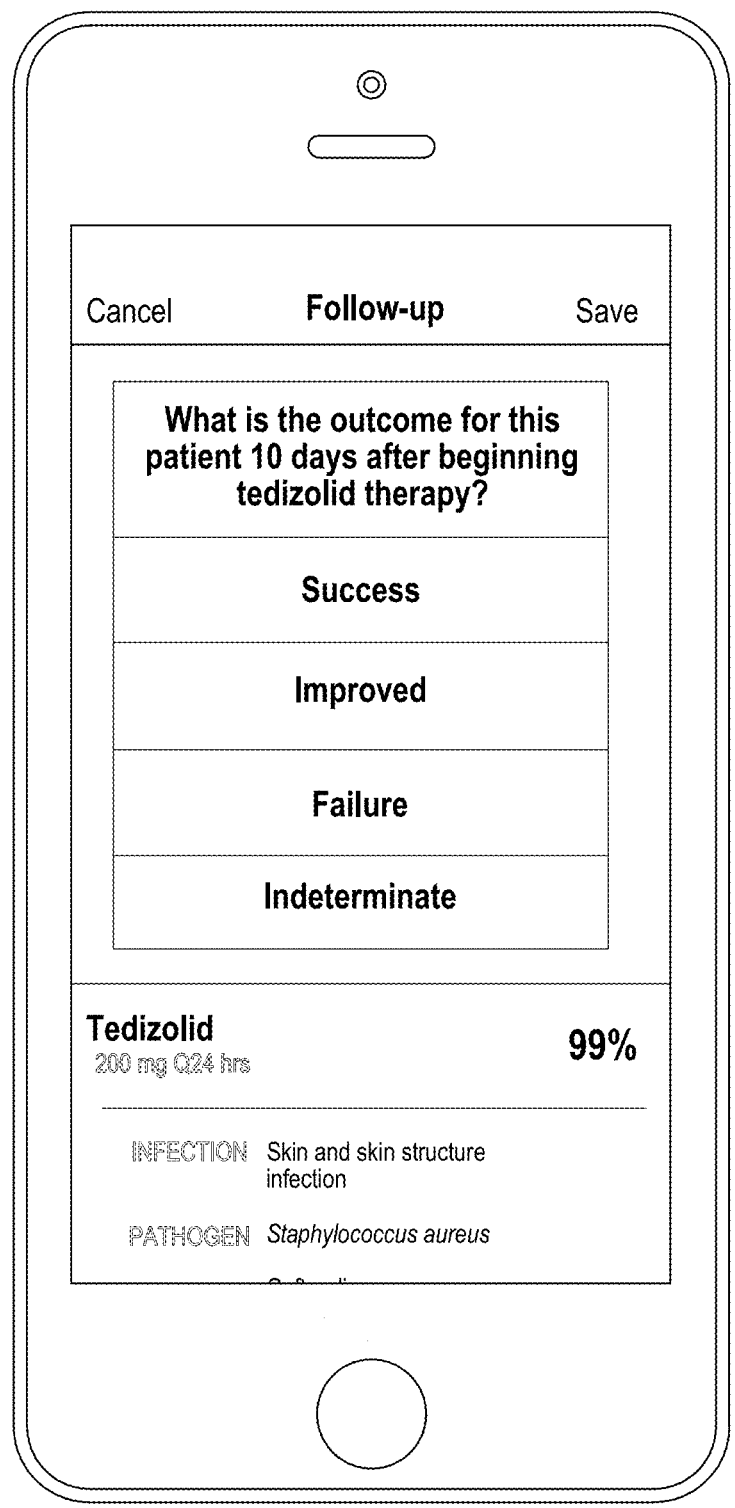

FIG. 19 is an example of a Follow-up screen that can be utilized in order to note the efficacy of the drug therapy when administered to the given patient. FIGS. 19-20 represent different types of questions/data that can be asked/collected by the program code in order to track the success of the selected treatment.

Figure 21:
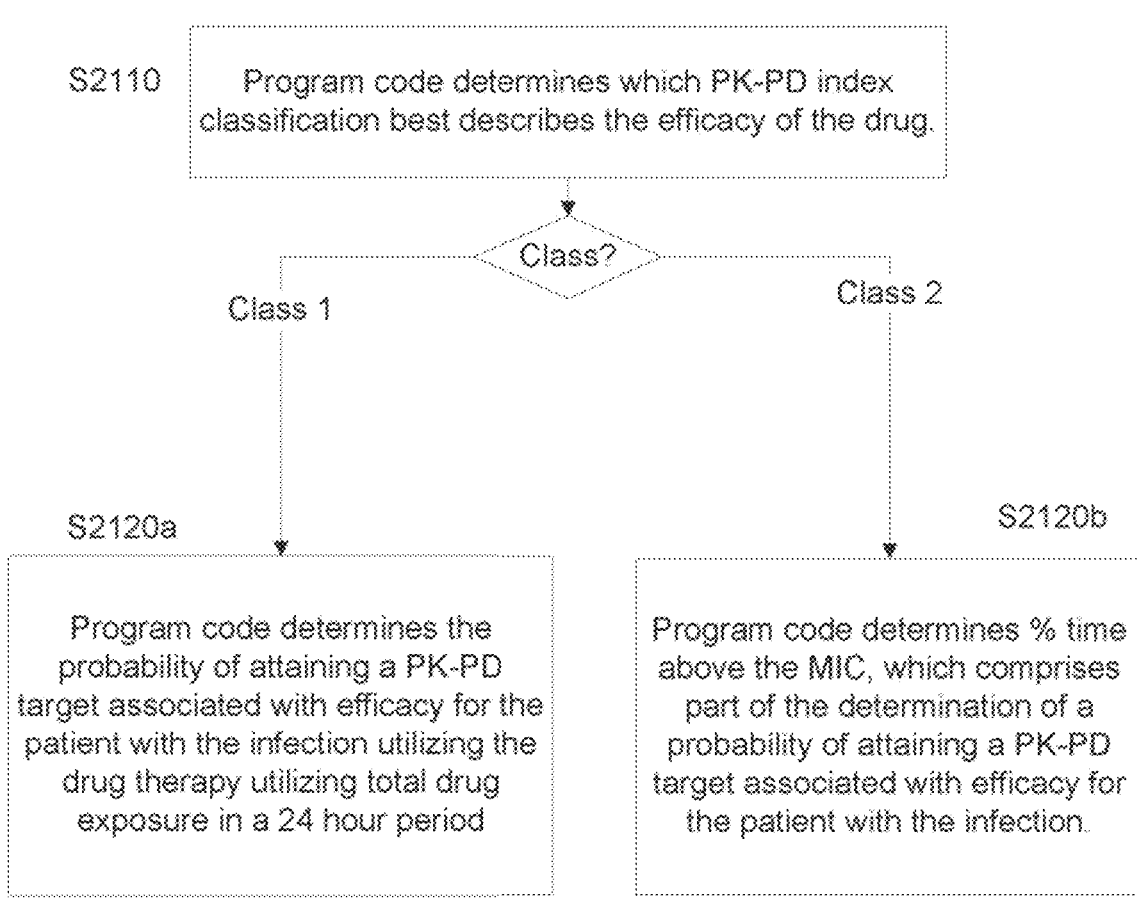
FIG. 21 depicts a workflow of an embodiment of the present invention.

As aforementioned when discussing FIG. 4, the program code selects a pharmacokinetic model to apply to determine the probability of attaining a PK-PD target associated with efficacy for a given drug therapy. The following sections provide examples of the models that can be applied in various embodiments of the present invention and how these models can be applied by the program code. FIG. 21 detail various determinations made by the program code in selecting and applying a pharmacokinetic model to a given drug therapy.

In an aspect of the present invention, in order to select the pharmacokinetic model, the program code first determines which PK-PD index classification best describes the efficacy of the drug. While there are more than two possible categories for this classification, as one example, FIG. 21 provides an example based on only two categories (S2110). In the first class, the probability of attaining the PK-PD target associated with efficacy for a drug therapy is determined at least in part, based upon the total drug exposure in a 24 hour period, wherein the AUC:MIC ratio is at least part of the determination (S2120a). In the second class, the % time above MIC is calculated and comprises at least a portion of the determination (S2120b). Despite the categorization of drugs into these two distinct classes by the program code, the model applied by the program code will differ between drugs. Depending upon a drug therapy selected, the program code may apply a customized model, including varying the parameters requested from a user, to ultimately determine the probabilities displayed. However, in embodiments of the present invention, the class to which the drug belongs directs the type of model utilized by the program code.

An example of one drug therapy that would be classified in the first category is ciprofloxacin. As aforementioned, the program code selects and applies the models based upon the drug therapy itself. However, the patient characteristics and MIC obtained by the program code affect the resulting prediction of PK-PD target attainment.

In the equations below, an estimated probability of attaining a PK-PD target associated with efficacy for ciprofloxacin is determined based upon parameters related to ciprofloxacin and obtained by the program code in the manner described in FIG. 4. The parameters obtained by the program include, but are not limited to, the drug therapy and dosage, which in the example below, the drug therapy is ciprofloxacin which is given every 8 hours intravenously. The patient characteristics are:

1) Creatinine clearance (CLcr): 63 mL/min; and
2) Weight (WT).

The MIC in the example below is 1 mg/L

Utilizing parameters, specific to ciprofloxacin, the program code determines the area under the curve over 24 hours ($AUC_{24}$). Equation 1 is an example of an Equation that the program code can utilize to make this determination. In the Equation 2, below, the $AUC_{24}$ is used to find the total clearance (CLt).

$$AUC_{24} = \frac{\text{Daily Dose}}{CLt} \qquad \text{(Equation 1)}$$

$$CLt = (0.00145 \times CLcr + 0.167) \times WT \qquad \text{(Equation 2)}$$

By applying the parameters discussed, the following calculations can be made:

$$\text{Daily Dose} = 400 \text{ mg}/8 \text{ hr} \times 24 \text{ hr} = 1200 \text{ mg}$$

$$CLt = (0.00145 \times 63 + 0.167) \times 70 = 18.1 \text{ L/hr}$$

$$AUC_{24} = 1200/18.1 = 66.4 \text{ mg/L} \times \text{hr}$$

$$AUC{:}MIC \text{ ratio} = \frac{AUC_{24}}{MIC} = \frac{66.4}{1} = 66.4$$

Once the AUC:MIC ratio is calculated, it is compared to the threshold for AUC:MIC ratio associated with efficacy (i.e., the PK-PD target). If it is above the PK-PD target, a patient is more likely to have a successful response to therapy; if it is below, the patient is less likely. A point estimate for probability of PK-PD target attainment will be determined as a function of the AUC:MIC ratio. The variability about this estimate is also determined by the program code. Thus, by obtaining parameters from a user and/or a memory resource, determining the relevant model, applying the model and using simulation, and returning a result to a user.

Returning to FIG. 21, if the drug therapy being evaluated by the program code is in the second class, the program code calculates the % time above the MIC, which comprises at least a portion of the determination (S2120b). As discussed earlier, in embodiments of the present invention, in order to predict the probability of attaining the PK-PD target associated with efficacy for a given drug therapy, the pharmacokinetic model applied depends upon the actual drug, so the program code determined what model to apply based upon the drug therapy. Meropenem is an example of a drug therapy that is a member of this class and is used as an example in explaining an example of a pharmacokinetic model applied to members of this PK-PD classification.

FIG. 22 is an example of the application of a pharmacokinetic model to determine the efficacy of the drug therapy for a given patient. Referring to FIG. 22, as explained earlier, the program code obtains patient characteristics, a MIC, and the drug therapy and dose parameters. The program code uses these parameters to compute the % time above MIC. To make this determination, the program code computes the Kcp, Kpc, and Kel values, the Alpha and Beta, the A and B and then, and uses these values to find the concentration during infusion, the concentration after infusion, and then applies these values to calculate a final efficacy percentage for the drug for the given patient. The derivation of these individual values is discussed below. The variables utilized in the present example are defined as follows: Kcp is the rate constant for flow from central to peripheral; Kpc is rate constant for flow from peripheral to central; Alpha is the rate constant for the first phase of drug elimination; Beta is the rate constant for the second phase of drug elimination; A is the concentration in the alpha phase at time 0; and B is the concentration in the beta phase at time 0.

FIG. 23 shows an example of a two compartment model that is utilized when evaluating meropenem. In the figure, the compartment with Vc stands for "volume of the central compartment" which is usually blood. Thus, when meropenem is infused (arrow with Ko), it will be inputted into this compartment. The second compartment, Vp, "peripheral compartment," is for tissue. The transfer rate of drug between these two compartments is called "distributional clearance" (CLd). In the central compartment, drug will be eliminated (by routes such as renal excretion or metabolism) and this is considered an output (arrow going out to nowhere) and is termed "total clearance" (CLt).

Using a steady state model and the two-compartment model for and the drug meropenem, the Equation 3 and Equation 4 can be applied.

$$fC(t) = f_{up} \times K_0 \left[ \frac{A}{\alpha}\left(1 - e^{-\alpha t} + e^{-\alpha \tau} \frac{(1 - e^{-\alpha T_{inf}})e^{-\alpha(t-T_{inf})}}{1 - e^{-\alpha \tau}}\right) + \frac{B}{\beta}\left(1 - e^{-\beta t} + e^{-\beta \tau} \frac{(1 - e^{-\beta T_{inf}})e^{-\beta(t-T_{inf})}}{1 - e^{-\beta \tau}}\right)\right] \quad \text{Equation 3}$$

$$fC(t) = f_{up} \times K_0 \quad \text{Equation 4}$$
$$\left[\frac{A}{\alpha}\left(\frac{(1 - e^{-\alpha T_{inf}})e^{-\alpha(t-T_{inf})}}{1 - e^{-\alpha \tau}}\right) + \frac{B}{\beta}\left(\frac{(1 - e^{-\beta T_{inf}})e^{-\beta(t-T_{inf})}}{1 - e^{-\beta \tau}}\right)\right]$$

Table 1 below includes the parameters utilized by the above equations.

TABLE 1

$$A = \frac{1}{Vc} \frac{\alpha - Kpc}{\alpha - \beta}$$

$$B = \frac{1}{Vc} \frac{\beta - Kpc}{\beta - \alpha}$$

TABLE 1-continued $$\alpha = \frac{1}{2}\left[(Kcp + Kpc + Kel) + \sqrt{(Kcp + Kpc + Kel)^2 - 4(Kpc)(Kel)}\right]$$

$$\beta = \frac{1}{2}\left[(Kcp + Kpc + Kel) - \sqrt{(Kcp + Kpc + Kel)^2 - 4(Kpc)(Kel)}\right]$$

$$Kcp = \frac{CLd}{Vc}$$

$$Kpc = \frac{CLd}{Vp}$$

$$Kel = \frac{CLt}{Vc}$$

Below are values that can be utilized in the present invention for meropenem. In an embodiment of the present invention, the values can be retained on a memory resource and identified and utilized by the program code upon the program code categorizing the drug by the PK-PD index and identifying the appropriate model.

For meropenem:

Vc (Liters)=10.8×(WT/70)

Vp (Liters)=12.6×(WT/70)

CLd (Liters/hour)=18.6×(WT/70)

CLt (Liters/hour)=(10.2+2.08×CLcr)×(WT/70)×0.06 fraction unbound (fup)=0.98

The variables utilized in the present example are defined as follows: Kcp is the rate constant for flow from central to peripheral; Kpc is the rate constant for flow from peripheral to central; Alpha is the rate constant for the first phase of drug elimination; Beta is the rate constant for the second phase of drug elimination; A is the concentration in the alpha phase at time 0; and B is the concentration in the beta phase at time 0.

An embodiment of the present invention can obtain the following drug and dose information: Dose=2000 milligrams; Duration of infusion ($T_{inf}$)=3 hours; $K_0$=Dose/$T_{inf}$=2000 mg/3 hr; Dosing interval ($\tau$)=8 hours. This embodiment can also obtain the following patient characteristics: Creatinine clearance (CLcr)=63.4 mL/min; Weight (WT)=86 kg. The present invention also obtains the following MIC: MIC=8 mg/L. Utilizing these values, the program code can determine Kcp, Kpc, and Kel values, the Alpha and Beta, the A and B and then, and uses these values to find the concentration during infusion, the concentration after infusion, and then applies these values to calculate the probability of attaining the PK-PD target associated with efficacy for the drug for the given patient. In this example, the program code returns the value of 99% for the probability of attaining the PK-PD target associated with efficacy for this drug with these parameters.

Figure 24:
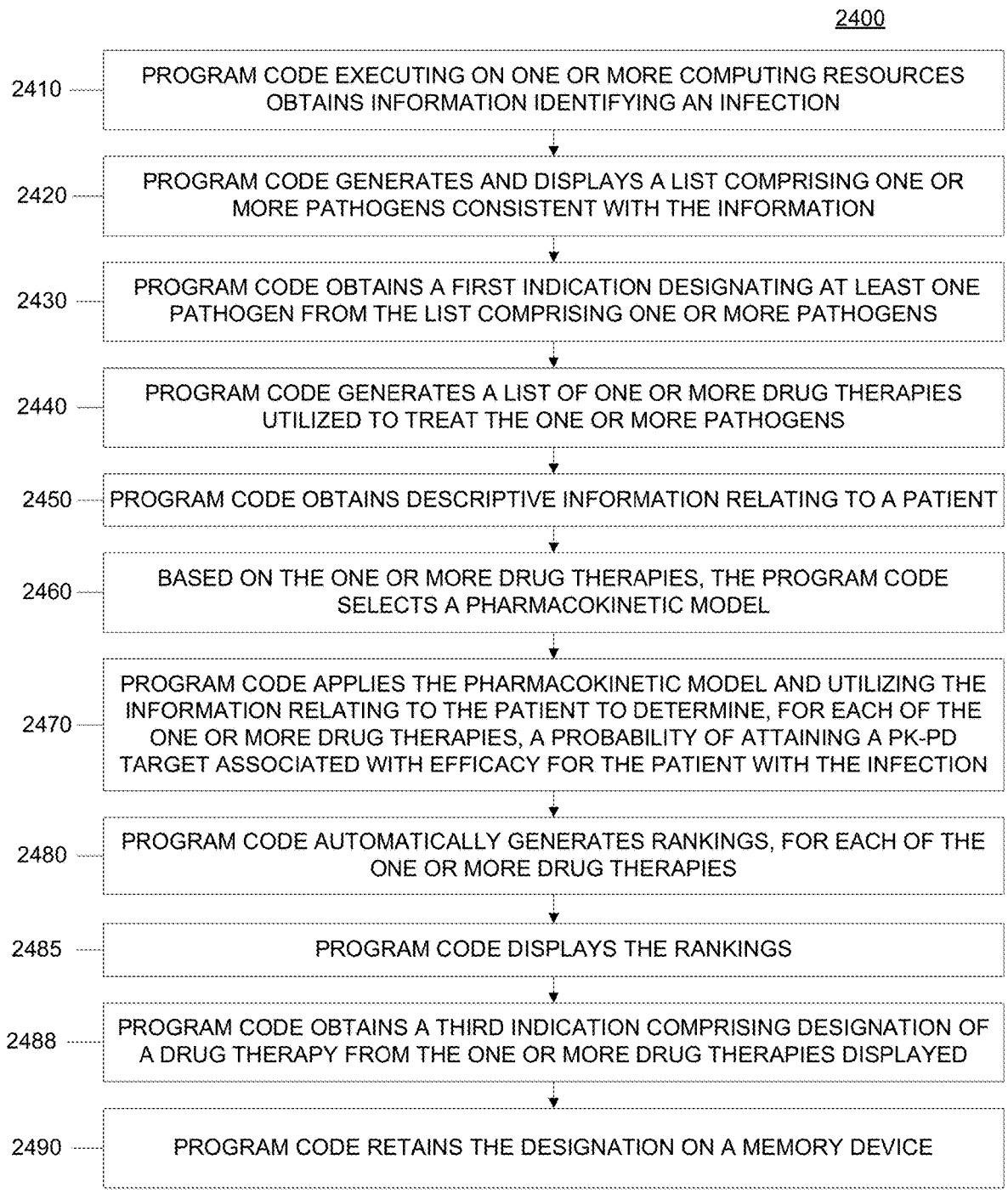
FIG. 24 is a workflow that illustrates various aspects of some embodiments of the present invention.

FIG. 24 is a workflow 2400 that illustrates certain aspects of some embodiments of the present invention utilized for determining a probability of attaining a PK-PD target associated with efficacy for a patient. In embodiment of the present invention, program code executing on one or more computing resources (including but not limited to one or more resources of a cloud computing environment), obtains information identifying an infection (2410). Based on the information, the program code generates and displays a list comprising one or more pathogens consistent with the information (2420). The program code obtains a first indication designating at least one pathogen from the list comprising one or more pathogens (2430). Based on at the obtaining the list, the program code generates a list of one or more drug therapies utilized to treat the one or more pathogens (2440). The program code obtains descriptive information relating to a patient (2450). The descriptive information can include, but is not limited to, an infection acquired by the patient, a pathogen isolated from the patient, a creatinine clearance of the patient, a weight of the patient, and a height of the patient.

In some embodiments of the present invention, the program code communicates with the patient and/or presents the patient (user) with an interface upon which to provide indications through a personal computing device that is an Internet of Things (IoT) device. This, the IoT device could passively and/or actively collect a certain portion of the descriptive information from the user. As understood by one of skill in the art, the Internet of Things (IoT) is a system of interrelated computing devices, mechanical and digital machines, objects, animals and/or people that are provided with unique identifiers and the ability to transfer data over a network, without requiring human-to-human or human-to-computer interaction. These communications are enabled by smart sensors, which include, but are not limited to, both active and passive radio-frequency identification (RFID) tags, which utilize electromagnetic fields to identify automatically and to track tags attached to objects and/or associated with objects and people. Smart sensors, such as RFID tags, can track environmental factors related to an object, including but not limited to, temperature and humidity. The smart sensors can be utilized to measure temperature, humidity, vibrations, motion, light, pressure and/or altitude. IoT devices also include individual activity and fitness trackers, which include (wearable) devices or applications that include smart sensors for monitoring and tracking fitness-related metrics such as distance walked or run, calorie consumption, and in some cases heartbeat and quality of sleep and include smartwatches that are synced to a computer or smartphone for long-term data tracking. Because the smart sensors in IoT devices carry unique identifiers, a computing system that communicates with a given sensor can identify the source of the information. Within the IoT, various devices can communicate with each other and can access data from sources available over various communication networks, including the Internet.

Returning to FIG. 24, in some embodiments of the present invention, based on the one or more drug therapies, the program code selects a pharmacokinetic model (2460). The program code applies the pharmacokinetic model and utilizing the information relating to the patient to determine, for each of the one or more drug therapies, a probability of attaining a PK-PD target associated with efficacy for the patient with the infection (2470). In some embodiments of the present invention, the program code automatically generates rankings, for each of the one or more drug therapies, by ordering each probability of attaining the PK-PD target associated with efficacy for the patient with the infection, for each of the one or more drug therapies, for the one or more drug therapies (2480). The program code displays the rankings (2485). The rankings are a ranked list with the probability of attaining a PK-PD target associated with efficacy for the patient with the infection for each of the one or more drug therapies, ranked in order of predicted efficacy. In some embodiments of the present invention, responsive to the displaying, the program code obtains a third indication comprising designation of a drug therapy from the one or more drug therapies displayed (2488). The program code retains the designation on a memory device (2490).

Figure 25:
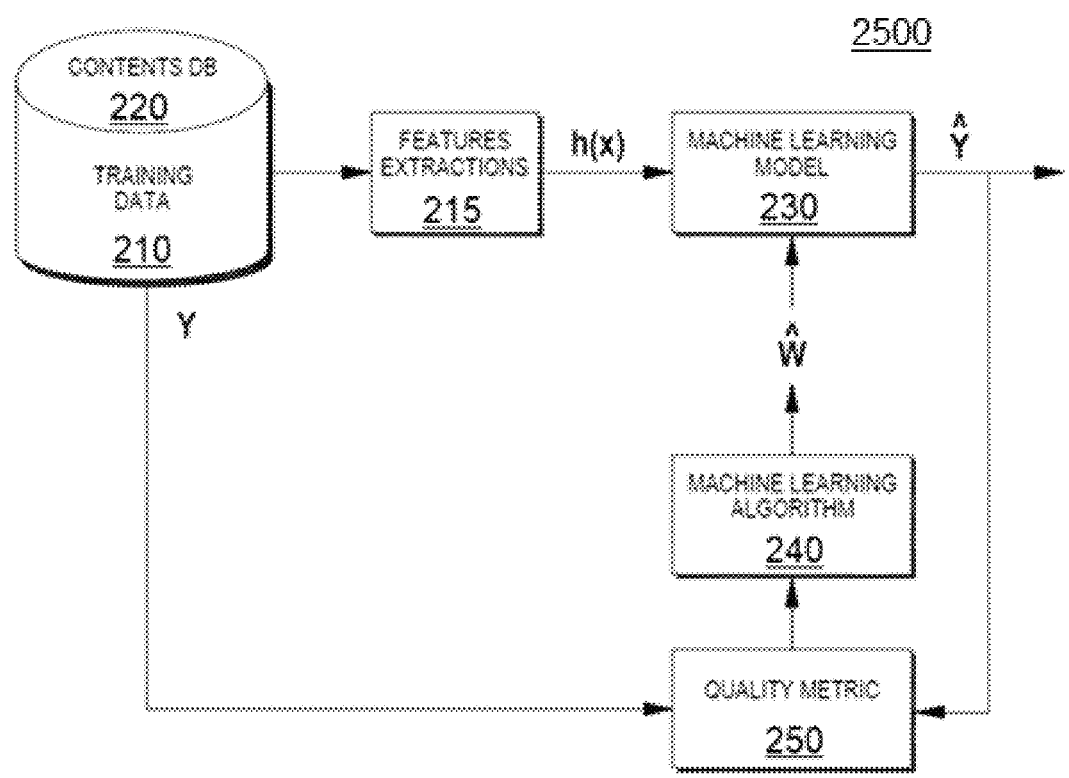
FIG. 25 is a workflow that illustrates various aspects of some embodiments of the present invention.

FIG. 25 illustrates various aspects of a machine learning technique that can be utilized in embodiments of the present invention to create and tune a base model utilized in embodiments of the present invention for determining a probability of attaining a PK-PD target associated with efficacy for a patient. In embodiments of the present invention, the base model describes a relationship between patient response and PK-PD target attainment that accounts for patient-specific response modifiers (e.g., previous antibiotic use, age, clearing organ function, etc.). As explained earlier, subsequent to a user providing a third indication comprising designation of a drug therapy from the one or more drug therapies displayed (e.g., FIG. 24, 2488) and the program code retaining the designation on a memory device (e.g., FIG. 24, 2490), the program code in embodiments of the present invention continues to obtain data regarding the success of the drug therapy, from the patient or provider utilizing the application, via an interface. As illustrated in FIGS. 18 and 20, the program code can generate a prompt in the interface to solicit information related to the results of a therapy selected by the user. As illustrated in FIG. 18, some embodiments of the present invention solicit this data at 72 hours after the user selects the given regimen, and also, at a later interval, such as 10 days, as illustrated in FIG. 20. These intervals are merely examples of set time periods at which feedback can be solicited by the program code. As the program code obtains the results of the selected therapies from the users, via a graphical user interface, in some embodiments of the present invention, the program code can identify various features/attributes (e.g., patterns) in this data, and utilize these results as training data 240, to further train a base model to better determine a probability of attaining a PK-PD target associated with efficacy for a patient for future patients. The base model describes a relationship between patient response and PK-PD target attainment that accounts for patient-specific response modifiers (e.g., previous antibiotic use, age, clearing organ function, etc.). In identifying these features/attributes, the program code can utilize various techniques including, but not limited to, mutual information, which is an example of a method that can be utilized to identify features in an embodiment of the present invention. Further embodiments of the present invention utilize varying techniques to select features (elements, patterns, attributes, etc.), including but not limited to, diffusion mapping, principal component analysis, recursive feature elimination (a brute force approach to selecting features), and/or a Random Forest, to select the features. The program code can utilize a machine learning algorithm 240 to train the machine learning model 230 (e.g., the algorithms utilized by the program code, referred to herein as a base model), including providing weights for the conclusions, so that the program code can prioritize various commonalities between patients, such that the program code can learn efficacy patterns based on patient attributes, in accordance with the predictor functions that comprise the machine learning model 230.

As discussed earlier, the base model describes a relationship between patient response and PK-PD target attainment that accounts for patient-specific response modifiers (e.g., previous antibiotic use, age, clearing organ function, etc.). The conclusions can be evaluated by a quality metric 250. Through cognitive analysis, the program code can determine (with increased accuracy based on the repeated use of the model) the probability of attaining a PK-PD target associated with efficacy for a patient, and thus, provide more accurate rankings for various drug therapies. In some embodiments of the present inventions, the personal attributes of the patients can be correlated by the program code such that results of a group of related (based on the analysis of the program code) patients can impact the predicted efficacy of a given drug treatment for a new patient, who shares relevant attributes with this group. Thus, with each new patient, that new patient's data will be used to estimate PK-PD target attainment and the associated the probability of a positive response to the (one or more) drug regimen. As illustrated in certain of the figures, the program code then orders the probabilities and provides then to the user through a graphical user interface.

In some embodiments of the present invention, in addition to the results (e.g., outcome data) provided by the users related to the patients (who may be the users or the clinicians treating the patients can be the users), to tune the base model, the program code utilizes as training data 240 aggregate patient demographic data, clinical data, and laboratory data. The program code can obtain portions of this data from a variety of publicly and privately available data sources. However, patient demographic data is solicited by the program code in some embodiments of the present invention and can be utilized to generate the base model.

Figure 26:
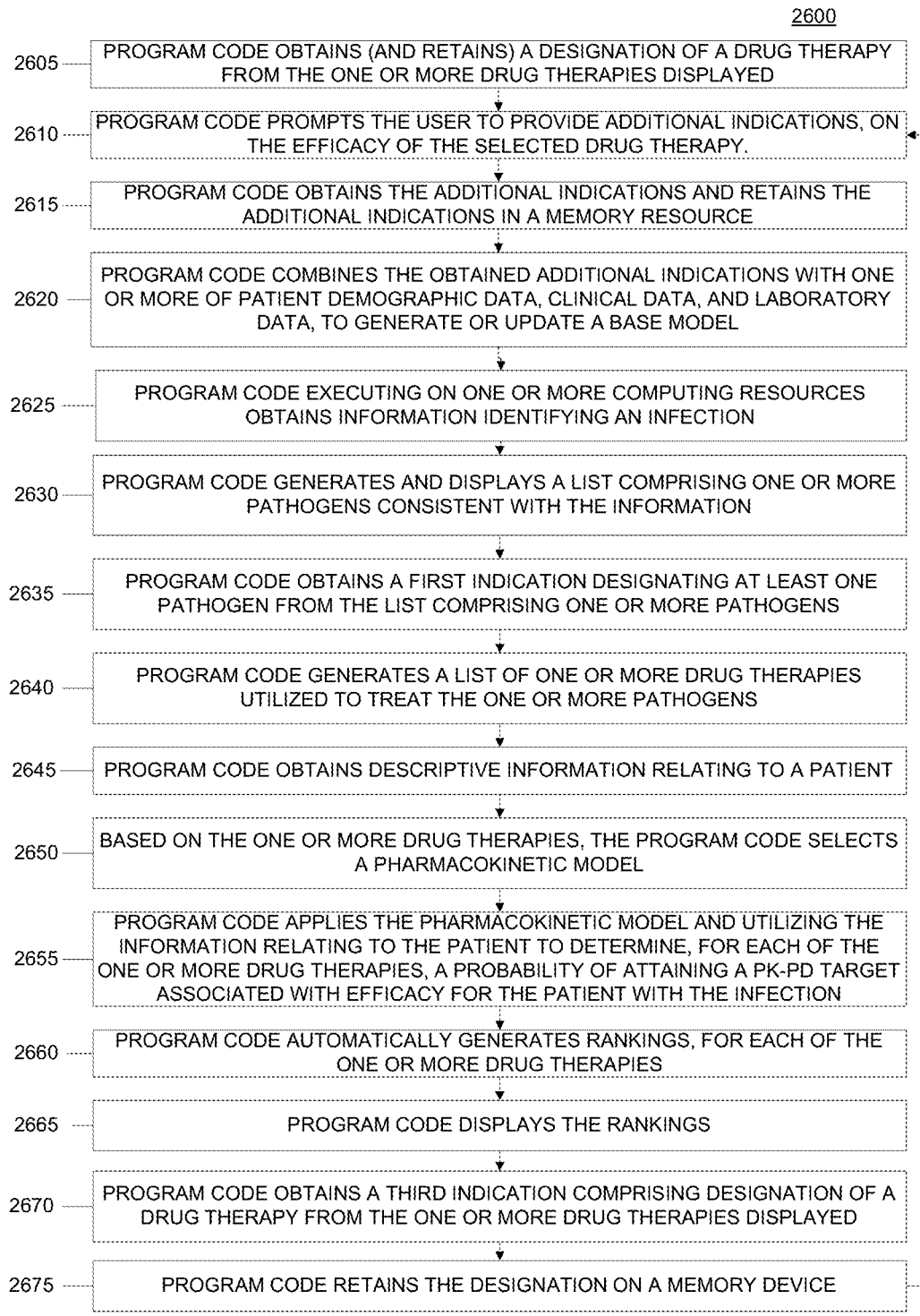

FIG. 26 is workflow 2600 that further illustrates the machine learning aspects of some embodiments of the present invention. In an embodiment of the present invention, upon display of the results (e.g., FIG. 15), which can be the rankings, where the rankings comprise a ranked list with the probability of attaining a PK-PD target associated with efficacy for the patient with an infection for each of the one or more drug therapies, ranked in order of predicted efficacy, a user (e.g., clinician) selects a regimen and the program code obtains and retains (in a memory) an indication of a selecting of the regimen, via a graphical user interface generated by the program code, on computing device, a designation of a drug therapy from the one or more drug therapies displayed (2605). Program code prompts the user, via the computing device, at one or more predefined intervals, to provide additional indications, via the user interface (2610). The prompts request feedback from the user on the efficacy of the selected regimen (e.g., drug therapy). In some embodiments of the present invention, the user is prompted for this entry whether or not an application comprising the graphical user interface utilized for entry is open on the computing device. The program code can generate a notification on a home screen of the computing device. In some embodiments of the present invention, the program code can communicate with the existing software executing on the computing device in order to trigger the software to provide the notification. In some embodiments of the present invention, when a user taps the notification, the application which the user utilizes for entry of the requested data is launched automatically on the computing device. In some embodiments of the present invention, the notification is a real-time push message. The program code obtains the additional indications and retains the additional indications in a memory resource (2615). The program code combines the obtained additional indications with one or more of patient demographic data, clinical data, and laboratory data, to generate or update a base model (2620). The base model describes a relationship between patient response and PK-PD target attainment that accounts for patient-specific response modifiers (e.g., previous antibiotic use, age, clearing organ function, etc.).

In an embodiment of the present invention, program code obtains information identifying an infection (2625). Based on the information, the program code generates and displays a list comprising one or more pathogens consistent with the information (2630). The program code obtains a first indication designating at least one pathogen from the list comprising one or more pathogens (2635). Based on at the obtaining the list, the program code generates a list of one or more drug therapies utilized to treat the one or more pathogens (2640). The program code obtains descriptive information relating to a patient, the descriptive information including, but not limited to, an infection acquired by the patient, a pathogen isolated from the patient, a creatinine clearance of the patient, a weight of the patient, and a height of the patient (2645). Based on the one or more drug therapies, the program code selects a pharmacokinetic model (2650). The program code applies the pharmacokinetic model and utilizing the information relating to the patient and the base model, to determine, for each of the one or more drug therapies, a probability of attaining a PK-PD target associated with efficacy for the patient with the infection (2655). In some embodiments of the present invention, the program code automatically generates rankings, for each of the one or more drug therapies, by ordering each probability of attaining the PK-PD target associated with efficacy for the patient with the infection, for each of the one or more drug therapies, for the one or more drug therapies (2660). The program code displays the rankings, wherein the rankings comprise a ranked list with the probability of attaining a PK-PD target associated with efficacy for the patient with the infection for each of the one or more drug therapies, ranked in order of predicted efficacy (2665). As displayed in FIG. 24, responsive to the displaying, the program code obtains a third indication comprising designation of a drug therapy from the one or more drug therapies displayed (2670). The program code retains the designation on a memory device (2675). As illustrated by the path of FIG. 26, the program code the prompts the user, via the computing device, at one or more predefined intervals, to provide additional indications, via the user interface (2610). And hence, the aspects continue to tune the base model and increase the accuracy of the predictions provided by the program code to the user. Thus, data (patient response, PK-PD target attainment, patient-specific response modifiers) from each new patient will be used by the program code to modify the base model.

Figure 27:
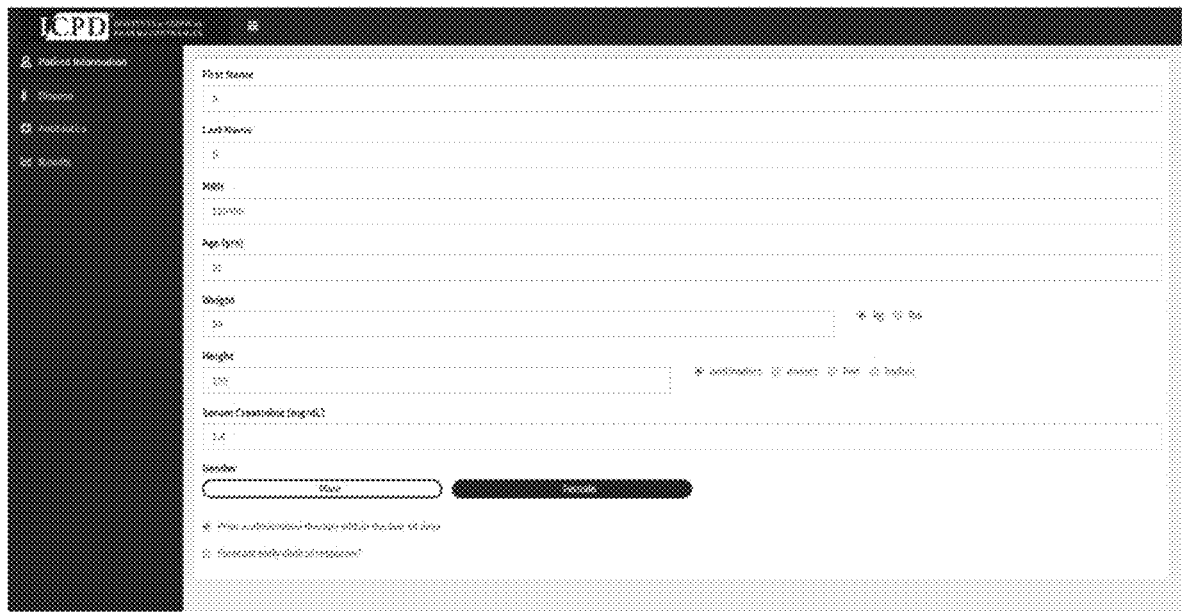
FIGS. 27-30C are examples of graphical user interfaces generated by the program code to prompt a user to provide information and to provide results to the user.
Figure 28:
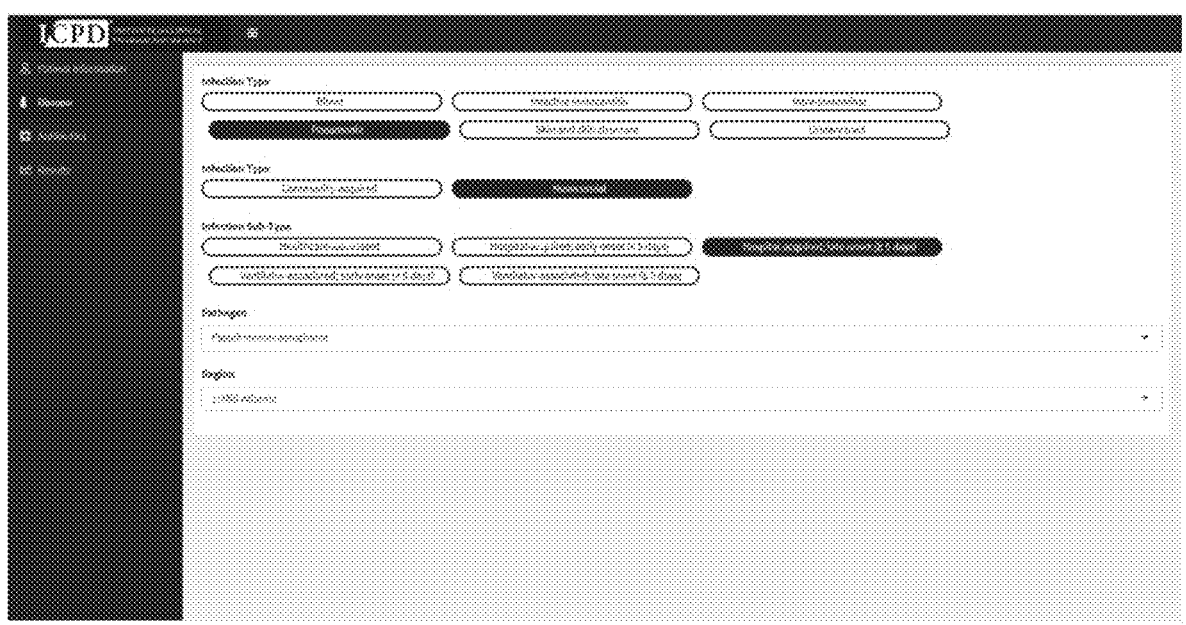
Figure 29:
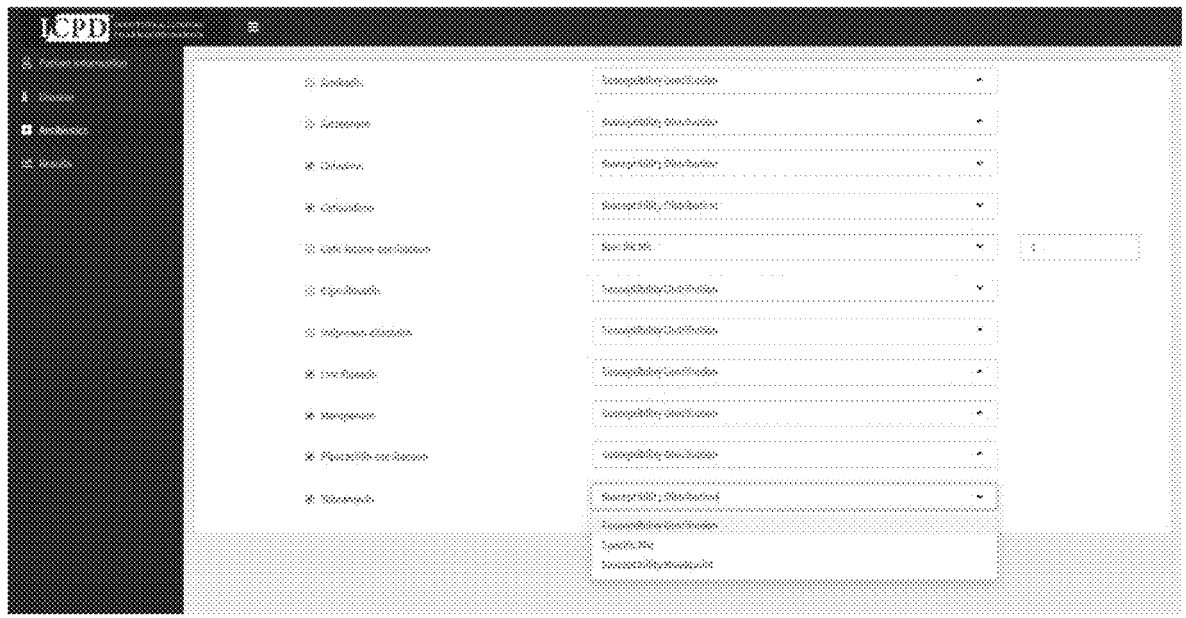
Figure 30A:
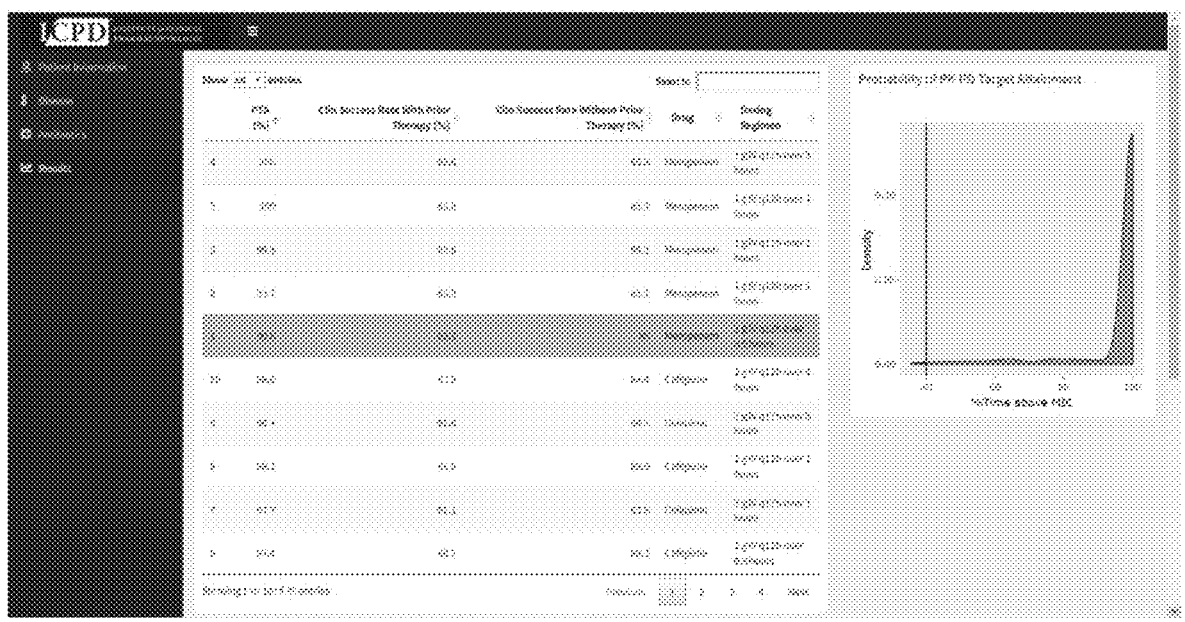
Figure 30B:
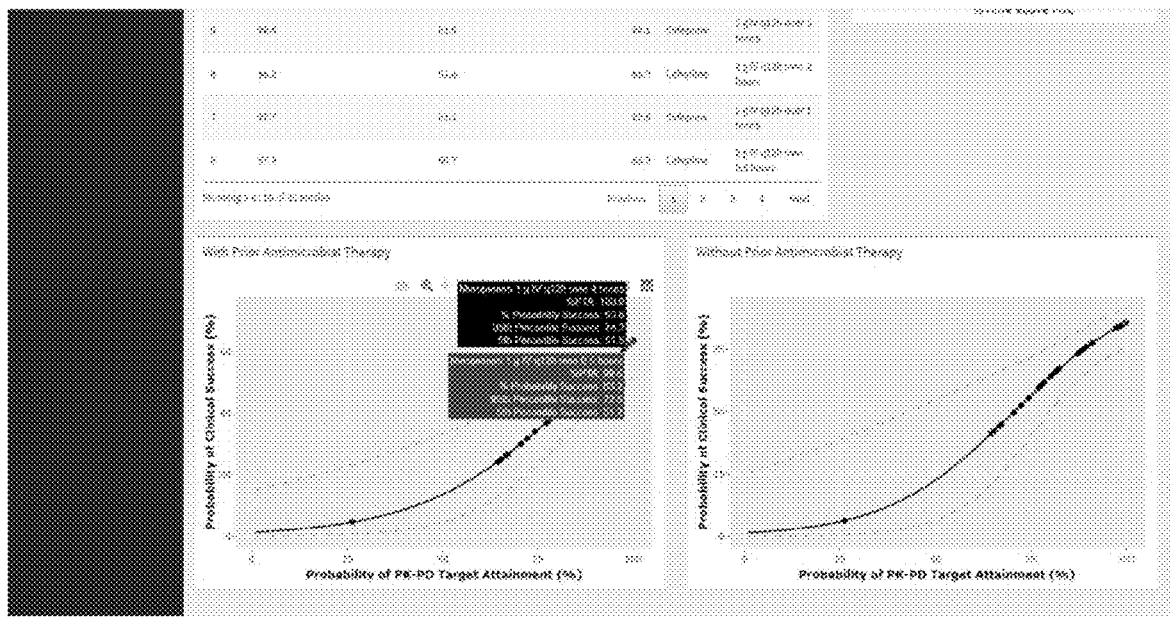
Figure 30C:
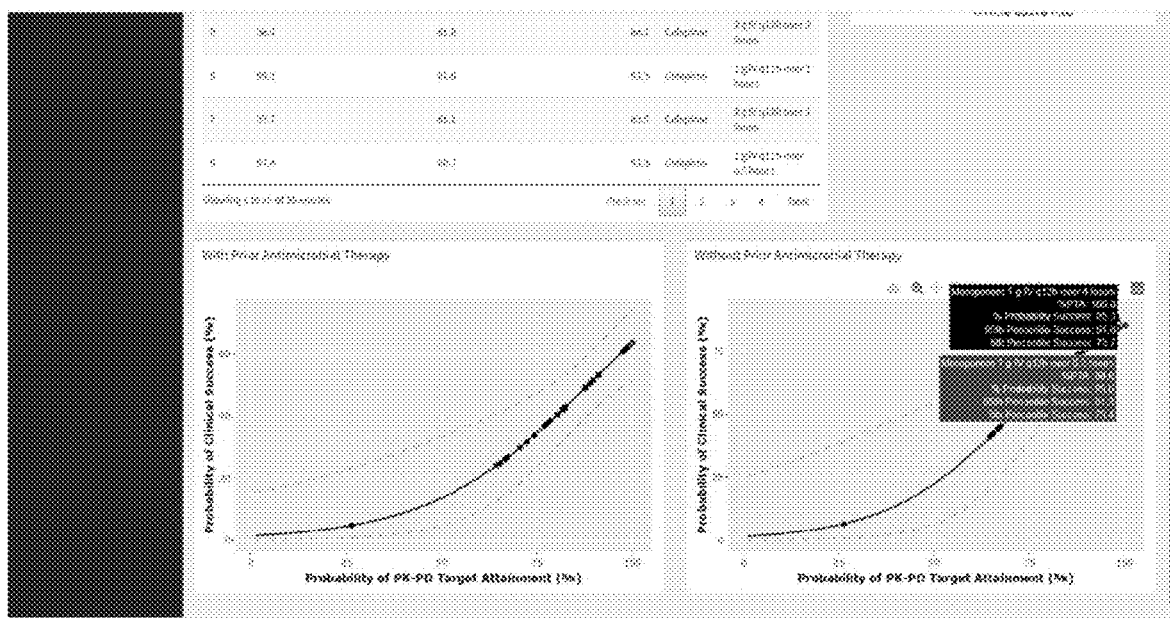

FIGS. 27-30C illustrate examples of graphical user interfaces generated by the program code in embodiments of the present invention on computing devices depict data utilized to generate and update the base model. For example, FIG. 27 illustrates an interface for entry demographic information of an individual utilizing and interface generated by program code executing on one or more processors. FIG. 28 illustrates and an interface in which a user identifies an infection. FIG. 29 is a list of drug regimens generated by the program code and the relevant mode in each case. Meanwhile, FIGS. 30A-30C illustrate probabilities of target attainment for one of the recommended drug regimens, the program code having completed an analysis utilizing, in part, the base model.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising", when used in this specification, specify the presence of stated features, integers, steps, operations, elements, and/or components, but do not preclude the presence or addition of one or more other features, integers, steps, operations, elements, components and/or groups thereof.

The corresponding structures, materials, acts, and equivalents of all means or step plus function elements in the descriptions below, if any, are intended to include any structure, material, or act for performing the function in combination with other elements as specifically noted. The description of the technique has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The invention claimed is:

1. A computer-implemented method comprising:
    obtaining, by one or more processors, information identifying an infection;
    based on the information, generating and displaying, by the one or more processors, a list comprising one or more pathogens consistent with the information;
    obtaining, by the one or more processors, a first indication designating at least one pathogen from the list comprising one or more pathogens;
    based on at the obtaining of the least one pathogen, generating, by the one or more processors, a list comprising one or more drug therapies utilized to treat the at least one pathogen;
    obtaining, by the one or more processors, descriptive information relating to a patient, the descriptive information comprising one or more data elements selected from the group consisting of: an infection acquired by the patient, a pathogen isolated from the patient, a creatinine clearance of the patient, a weight of the patient, and a height of the patient;
    based on the one or more drug therapies, selecting a pharmacokinetic model;
    applying, by the one or more processors, the pharmacokinetic model and utilizing the information relating to the patient to determine, for each of the one or more drug therapies, a probability of attaining a PK-PD target associated with efficacy for the patient with the infection;
    automatically generating, by the one or more processors, rankings, for each of the one or more drug therapies, by ordering each probability of attaining the PK-PD target associated with efficacy for the patient with the infection, for each of the one or more drug therapies, for the one or more drug therapies;
    displaying, by the one or more processors, the rankings, wherein the rankings comprise a ranked list with the probability of attaining a PK-PD target associated with efficacy for the patient with the infection for each of the one or more drug therapies, ranked in order of predicted efficacy;
    responsive to the displaying, obtaining, by the one or more processors, a third indication comprising designation of a drug therapy from the one or more drug therapies displayed;
    retaining by the one or more processors, the designation on a memory device;
    prompting, by the one or more processors, through a user interface, a user to provide data indicating an actual efficacy of the drug therapy as utilized by the patient with the infection at one or more predetermined intervals after obtaining the designation; and
    obtaining, by the one or more processors, responsive to the prompting, the data indicating the actual efficacy of the drug therapy.

2. The computer-implemented method of claim 1, further comprising:
    generating or updating, by the one or more processors, based on data comprising the data indicating the actual efficacy, a base model, wherein the base model describes a relationship between given patient response and PK-PD target attainment that accounts based on patient-specific response modifiers.

3. The computer-implemented method of claim 2, wherein the data further comprises data selected from the group consisting of: patient demographic data, clinical data, and laboratory data.

4. The computer-implemented method of claim 1, further comprising:
    obtaining, by the one or more processors, a second indication designating at least one drug therapy from the list comprising one or more drug, wherein the each of the one or more drug therapies utilized in the selecting and the applying is limited to the at least one drug therapy comprising the second indication.

5. The computer-implemented method of claim 1, wherein the selecting comprises:
    for each of the one or more drug therapies, determining a class for a PK-PD index;
    based on determining that a drug therapy of the one or more drug therapies is in a first class, selecting a pharmacokinetic model, wherein applying the pharmacokinetic model comprises evaluating total drug exposure in a 24 hour period, for the drug therapy, to determine the probability of attaining a PK-PD target associated with efficacy for the patient with the infection; and
    based on determining that a drug therapy of the one or more drug therapies is in a second class, selecting a pharmacokinetic model, wherein applying the pharmacokinetic model comprises evaluating % time above MIC, for the drug therapy, to determine the probability of attaining a PK-PD target associated with efficacy for the patient with the infection.

6. The computer-implemented method of claim 1, further comprising:
    displaying, by the one or more processors, a follow up option; and
    responsive to obtaining a positive response to the follow up option, presenting a reminder to follow up with the patient on a graphical user interface.

7. The computer-implemented method of claim 2, further comprising:
    obtaining, by one or more processors, additional information identifying an infection;
    based on the additional information, generating and displaying, by the one or more processors, a second list comprising one or more pathogens consistent with the additional information;
    obtaining, by the one or more processors, a first indication designating at least one pathogen from the second list comprising one or more pathogens from the second list;
    based on at the obtaining of the least one pathogen from the second list, generating, by the one or more processors, a third list comprising one or more drug therapies utilized to treat the at least one pathogen;

obtaining, by the one or more processors, descriptive information relating to a second patient, the descriptive information comprising one or more data elements selected from the group consisting of: an infection acquired by the second patient, a pathogen isolated from the second patient, a creatinine clearance of the second patient, a weight of the second patient, and a height of the second patient;

based on the one or more drug therapies in the third list, selecting a give pharmacokinetic model;

applying, by the one or more processors, the given pharmacokinetic model and utilizing the information relating to the second patient and the base model to determine, for each of the one or more drug therapies of the third list, a probability of attaining a PK-PD target associated with efficacy for the second patient with the infection;

automatically generating, by the one or more processors, current rankings, for each of the one or more drug therapies of the third list, by ordering each probability of attaining the PK-PD target associated with efficacy for the second patient with the infection, for each of the one or more drug therapies of the third list, for the one or more drug therapies of the third list; and displaying, by the one or more processors, the current rankings, wherein the current rankings comprise a ranked list with the probability of attaining a PK-PD target associated with efficacy for the second patient with the infection for each of the one or more drug therapies of the third list, ranked in order of predicted efficacy.

8. The computer-implemented method of claim 7, further comprising:

responsive to the displaying, obtaining, by the one or more processors, a fourth indication comprising a new designation of a drug therapy from the one or more drug therapies displayed for the second patient;

retaining by the one or more processors, the new designation of the drug therapy from the one or more drug therapies displayed for the second patient on a memory device;

prompting, by the one or more processors, through a user interface, a user to provide data indicating an actual efficacy of the drug therapy from the one or more drug therapies displayed for the second patient, as utilized by the second patient with the infection at one or more predetermined intervals after obtaining the new designation;

obtaining, by the one or more processors, responsive to the prompting, the data indicating the actual efficacy of the drug therapy from the one or more drug therapies displayed for the second patient; and updating, by the one or more processors, based on data comprising the data indicating the actual efficacy of the drug therapy from the one or more drug therapies displayed for the second patient, the base model.

9. The computer-implemented method of claim 2, wherein the patient-specific response modifiers are selected from the group consisting of: previous antibiotic use, age, and clearing organ function.

10. A computer system comprising:

a memory; and one or more processors in communications with the memory, wherein the computer system is configured to perform a method, the method comprising:

obtaining, by the one or more processors, information identifying an infection;

based on the information, generating and displaying, by the one or more processors, a list comprising one or more pathogens consistent with the information;

obtaining, by the one or more processors, a first indication designating at least one pathogen from the list comprising one or more pathogens;

based on at the obtaining of the least one pathogen, generating, by the one or more processors, a list comprising one or more drug therapies utilized to treat the at least one pathogen;

obtaining, by the one or more processors, descriptive information relating to a patient, the descriptive information comprising one or more data elements selected from the group consisting of: an infection acquired by the patient, a pathogen isolated from the patient, a creatinine clearance of the patient, a weight of the patient, and a height of the patient;

based on the one or more drug therapies, selecting a pharmacokinetic model;

applying, by the one or more processors, the pharmacokinetic model and utilizing the information relating to the patient to determine, for each of the one or more drug therapies, a probability of attaining a PK-PD target associated with efficacy for the patient with the infection;

automatically generating, by the one or more processors, rankings, for each of the one or more drug therapies, by ordering each probability of attaining the PK-PD target associated with efficacy for the patient with the infection, for each of the one or more drug therapies, for the one or more drug therapies;

displaying, by the one or more processors, the rankings, wherein the rankings comprise a ranked list with the probability of attaining a PK-PD target associated with efficacy for the patient with the infection for each of the one or more drug therapies, ranked in order of predicted efficacy;

responsive to the displaying, obtaining, by the one or more processors, a third indication comprising designation of a drug therapy from the one or more drug therapies displayed;

retaining by the one or more processors, the designation on a memory device;

prompting, by the one or more processors, through a user interface, a user to provide data indicating an actual efficacy of the drug therapy as utilized by the patient with the infection at one or more predetermined intervals after obtaining the designation; and obtaining, by the one or more processors, responsive to the prompting, the data indicating the actual efficacy of the drug therapy.

11. The computer system of claim 10, the method further comprising:

generating or updating, by the one or more processors, based on data comprising the data indicating the actual efficacy, a base model, wherein the base model describes a relationship between given patient response and PK-PD target attainment that accounts based on patient-specific response modifiers.

12. The computer system of claim 11, wherein the data further comprises data selected from the group consisting of: patient demographic data, clinical data, and laboratory data.

13. The computer system of claim 10, the method further comprising:
obtaining, by the one or more processors, a second indication designating at least one drug therapy from the list comprising one or more drug, wherein the each of the one or more drug therapies utilized in the selecting and the applying is limited to the at least one drug therapy comprising the second indication.

14. The computer system of claim 10, wherein the selecting comprises:
for each of the one or more drug therapies, determining a class;
based on determining that a drug therapy of the one or more drug therapies is in a first class, selecting a pharmacokinetic model, wherein applying the pharmacokinetic model comprises evaluating total drug exposure in a 24 hour period, for the drug therapy, to determine the probability of attaining a PK-PD target associated with efficacy for the patient with the infection; and
based on determining that a drug therapy of the one or more drug therapies is in a second class, selecting a pharmacokinetic model, wherein applying the pharmacokinetic model comprises evaluating % time above MIC, for the drug therapy, to determine the probability of attaining a PK-PD target associated with efficacy for the patient with the infection.

15. The computer system of claim 11, the method further comprising:
obtaining, by one or more processors, additional information identifying an infection;
based on the additional information, generating and displaying, by the one or more processors, a second list comprising one or more pathogens consistent with the additional information;
obtaining, by the one or more processors, a first indication designating at least one pathogen from the second list comprising one or more pathogens from the second list;
based on at the obtaining of the least one pathogen from the second list, generating, by the one or more processors, a third list comprising one or more drug therapies utilized to treat the at least one pathogen;
obtaining, by the one or more processors, descriptive information relating to a second patient, the descriptive information comprising one or more data elements selected from the group consisting of: an infection acquired by the second patient, a pathogen isolated from the second patient, a creatinine clearance of the second patient, a weight of the second patient, and a height of the second patient;
based on the one or more drug therapies in the third list, selecting a give pharmacokinetic model;
applying, by the one or more processors, the given pharmacokinetic model and utilizing the information relating to the second patient and the base model to determine, for each of the one or more drug therapies of the third list, a probability of attaining a PK-PD target associated with efficacy for the second patient with the infection;
automatically generating, by the one or more processors, current rankings, for each of the one or more drug therapies of the third list, by ordering each probability of attaining the PK-PD target associated with efficacy for the second patient with the infection, for each of the one or more drug therapies of the third list, for the one or more drug therapies of the third list; and
displaying, by the one or more processors, the current rankings, wherein the current rankings comprise a ranked list with the probability of attaining a PK-PD target associated with efficacy for the second patient with the infection for each of the one or more drug therapies of the third list, ranked in order of predicted efficacy.

16. The computer system of claim 15, further comprising:
responsive to the displaying, obtaining, by the one or more processors, a fourth indication comprising a new designation of a drug therapy from the one or more drug therapies displayed for the second patient;
retaining by the one or more processors, the new designation of the drug therapy from the one or more drug therapies displayed for the second patient on a memory device;
prompting, by the one or more processors, through a user interface, a user to provide data indicating an actual efficacy of the drug therapy from the one or more drug therapies displayed for the second patient, as utilized by the second patient with the infection at one or more predetermined intervals after obtaining the new designation;
obtaining, by the one or more processors, responsive to the prompting, the data indicating the actual efficacy of the drug therapy from the one or more drug therapies displayed for the second patient; and
updating, by the one or more processors, based on data comprising the data indicating the actual efficacy of the drug therapy from the one or more drug therapies displayed for the second patient, the base model.

17. The computer system of claim 11, wherein the patient-specific response modifiers are selected from the group consisting of: previous antibiotic use, age, and clearing organ function.

18. The computer system of claim 10, the method further comprising:
displaying, by the one or more processors, a follow up option; and
responsive to obtaining a positive response to the follow up option, displaying a reminder to follow up with the patient on a graphical user interface.

19. A computer program product comprising:
a computer readable storage medium readable by a processing circuit and storing instructions for execution by the processing circuit for performing a method comprising:
obtaining, by the one or more processors, information identifying an infection;
based on the information, generating and displaying, by the one or more processors, a list comprising one or more pathogens consistent with the information;
obtaining, by the one or more processors, a first indication designating at least one pathogen from the list comprising one or more pathogens;
based on at the obtaining of the least one pathogen, generating, by the one or more processors, a list comprising one or more drug therapies utilized to treat the at least one pathogen;
obtaining, by the one or more processors, descriptive information relating to a patient, the descriptive information comprising one or more data elements selected from the group consisting of: an infection acquired by the patient, a pathogen isolated from the patient, a creatinine clearance of the patient, a weight of the patient, and a height of the patient;

based on the one or more drug therapies, selecting a pharmacokinetic model;

applying, by the one or more processors, the pharmacokinetic model and utilizing the information relating to the patient to determine, for each of the one or more drug therapies, a probability of attaining a PK-PD target associated with efficacy for the patient with the infection;

automatically generating, by the one or more processors, rankings, for each of the one or more drug therapies, by ordering each probability of attaining the PK-PD target associated with efficacy for the patient with the infection, for each of the one or more drug therapies, for the one or more drug therapies;

displaying, by the one or more processors, the rankings, wherein the rankings comprise a ranked list with the probability of attaining a PK-PD target associated with efficacy for the patient with the infection for each of the one or more drug therapies, ranked in order of predicted efficacy;

responsive to the displaying, obtaining, by the one or more processors, a third indication comprising designation of a drug therapy from the one or more drug therapies displayed;

retaining by the one or more processors, the designation on a memory device;

prompting, by the one or more processors, through a user interface, a user to provide data indicating an actual efficacy of the drug therapy as utilized by the patient with the infection at one or more predetermined intervals after obtaining the designation; and obtaining, by the one or more processors, responsive to the prompting, the data indicating the actual efficacy of the drug therapy.

* * * * *